(12) United States Patent
Kim

(10) Patent No.: US 10,561,561 B2
(45) Date of Patent: Feb. 18, 2020

(54) FUNCTIONAL PILLOW FOR MANIPULATION THERAPY

(71) Applicants: T&I CO., LTD., Namyangju-si, Hyeonggi-do (KR); Hee Soo Kim, Hanam-si, Gyeonggi-do (KR)

(72) Inventor: Hee Soo Kim, Hanam-si (KR)

(73) Assignees: T&I CO., LTD., Namyangju-si, Gyeonggi-do (KR); Hee Soo Kim, Hanam-si, Gyeonggi-do (KR)

( * ) Notice: Subject to any disclaimer, the term of this patent is extended or adjusted under 35 U.S.C. 154(b) by 406 days.

(21) Appl. No.: 15/410,777

(22) Filed: Jan. 20, 2017

(65) Prior Publication Data

US 2017/0128307 A1     May 11, 2017

Related U.S. Application Data

(63) Continuation-in-part of application No. PCT/KR2014/011010, filed on Nov. 17, 2014.

(30) Foreign Application Priority Data

Jul. 24, 2014    (KR) .................. 10-2014-0093866

(51) Int. Cl.
    *A47G 9/10*          (2006.01)
    *A61H 1/00*          (2006.01)
              (Continued)

(52) U.S. Cl.
CPC .............. *A61H 1/008* (2013.01); *A47G 9/10* (2013.01); *A47G 9/109* (2013.01); *A61F 5/04* (2013.01); *A61H 7/001* (2013.01); *A47G 2009/1018* (2013.01); *A61H 2201/0134* (2013.01); *A61H 2201/1604* (2013.01); *A61H 2201/1609* (2013.01); *A61H 2201/1614* (2013.01); *A61H 2201/1645* (2013.01); *A61H 2203/0456* (2013.01)

(58) Field of Classification Search
CPC ...... A47G 9/10; A47G 9/1072; A47G 9/1081; A47G 9/109; A61H 1/008; A61H 7/001
USPC .................................... 5/636, 637; 128/845
See application file for complete search history.

(56) References Cited

U.S. PATENT DOCUMENTS

| | | | |
|---|---|---|---|
| 4,494,261 | A | 1/1985 | Morrow |
| 4,550,458 | A | 11/1985 | Fiore |

(Continued)

FOREIGN PATENT DOCUMENTS

| | | |
|---|---|---|
| CN | 101589988 A | 12/2009 |
| CN | 202843099 U | 4/2013 |

(Continued)

OTHER PUBLICATIONS

International Search Report for PCT/KR2014/011010 dated Apr. 17, 2015 from Korean Intellectual Property Office.

*Primary Examiner* — Keri J Nelson
(74) *Attorney, Agent, or Firm* — Revolution IP, PLLC

(57) ABSTRACT

Disclosed is a functional pillow for manipulation therapy, the functional pillow comprising: an occipital region accommodating portion which accommodates and supports an occipital region; a cervical vertebrae support portion which extends from the occipital region accommodating portion and supports cervical vertebrae; and a fourth ventricle expanding protrusion which protrudes from the occipital region accommodating portion.

7 Claims, 18 Drawing Sheets

(51) Int. Cl.
 *A61H 7/00* (2006.01)
 *A61F 5/04* (2006.01)

(56) References Cited

U.S. PATENT DOCUMENTS

| | | | |
|---|---|---|---|
| 5,778,469 A | 7/1998 | Festa | |
| 7,331,631 B1 * | 2/2008 | Yeh | A47C 7/38 |
| | | | 297/391 |
| 2013/0047339 A1 | 2/2013 | Kim | |

FOREIGN PATENT DOCUMENTS

| KR | 20-2011-0007957 U | 8/2011 |
|---|---|---|
| KR | 10-2012-0005893 A | 4/2015 |

* cited by examiner

FUNCTIONAL PILLOW FOR MANIPULATION THERAPY

CROSS REFERENCE TO PRIOR APPLICATIONS

This application is a Continuation-In-Part Application of International application PCT/KR2014/011010 filed on Nov. 17, 2014, which claims priority to Korean application 10-2014-0093866 filed on Jul. 24, 2014.

TECHNICAL FIELD

The present invention relates to a functional pillow for manipulation therapy, and more particularly, to a functional pillow for manipulation therapy which may induce circulation of a cerebrospinal fluid by applying expansion of the fourth ventricle and compression of the fourth ventricle of a craniosacral therapy, and may correct cervical vertebrae by using distraction.

BACKGROUND ART

Cervical vertebrae are bone structures positioned between cranial bones and thoracic vertebrae of a vertebral column, and defining a neck portion. The cervical vertebrae of a human include seven vertebrae. The cervical vertebrae allow a number of nerves to be smoothly connected to the brain, and support the heavy cranial bones. The most stable structure of the cervical vertebrae for performing the functions has a C-shaped curve, but a straight structure of the cervical vertebrae, which is caused by an inappropriate posture, results in problems of hypertension, chronic headache, cervical herniated nucleus pulpusus disc, and cervical vertebrae pain. The reason is that in the case of the straight structure of the cervical vertebrae, a weight of the head is concentrated at the cervical vertebrae, and intervals between discs gradually become narrower, and as a result, the nerves are easily compressed.

However, the cervical vertebrae of modern people may be easily deformed due to an excessive use of a PC and a mobile device. Therefore, it is important to periodically correct the cervical vertebrae of the modern people, and to relax strained muscles at the periphery of the cervical vertebrae.

Meanwhile, a human body has 'a flexion phase in which the cerebrospinal fluid is created and the cranial bones are expanded' and 'an extension phase in which the creation of the cerebrospinal fluid is stopped and the cranial bones are contracted', and in this case, a therapy, which initializes (hereinafter, referred to as "a still point") the circulation of the cerebrospinal fluid by interrupting the movement of the extension phase or the flexion phase, thereby normalizing a flow of the cerebrospinal fluid circulating between the cranial bones and sacral vertebrae, is called a craniosacral therapy.

However, the correction of the cervical vertebrae and the procedure of the craniosacral therapy are required to be carried out by special physical therapists, and as a result, there is a problem in that it is impossible for an ordinary person to perform a self-treatment.

SUMMARY OF THE INVENTION

The problems to be solved by the present invention are as follows.

First, an object of the present invention is to autonomously correct cervical vertebrae and induce a still point state regardless of time and place.

Second, another object of the present invention is to provide a functional pillow having functions of correcting cervical vertebrae and inducing a still point, thereby allowing a user to be naturally subjected to a treatment during sleep.

Third, still another object of the present invention is to provide a functional pillow capable of obtaining a distraction effect by applying force, in different directions, to shoulders, cervical vertebrae, and the head.

Technical problems of the present invention are not limited to the aforementioned technical problems, and other technical problems, which are not mentioned above, may be clearly understood by those skilled in the art from the following descriptions.

To achieve the objects, a functional pillow for manipulation therapy according to an exemplary embodiment of the present invention includes: an occipital region accommodating portion which accommodates and supports an occipital region; a cervical vertebrae support portion which extends from the occipital region accommodating portion and supports cervical vertebrae; and a fourth ventricle expanding protrusion which protrudes from the occipital region accommodating portion.

A functional pillow for manipulation therapy according to another exemplary embodiment of the present invention includes: a fourth ventricle compressing protrusion which inhibits left and right sides of an occipital bone from further expanding in a flexion phase in which the left and right sides of the occipital bone expand when a cerebrospinal fluid is created; a fourth ventricle expanding protrusion which inhibits an external occipital protuberance of the occipital bone from further protruding in an extension phase in which the external occipital protuberance of the occipital bone protrudes when the creation of the cerebrospinal fluid is stopped; and an occipital region accommodating portion which fixedly supports an occipital region, and is formed with the fourth ventricle compressing protrusion and the fourth ventricle expanding protrusion at a surface facing the occipital bone.

A functional pillow for manipulation therapy according to still another exemplary embodiment of the present invention includes: an occipital region accommodating portion which accommodates and supports an occipital region; a cervical vertebrae support portion which is formed to be inclined and supports cervical vertebrae; and lateral support portions which are formed at left and right sides of the cervical vertebrae support portion and the occipital region accommodating portion, respectively, and support a user's head when the user lies on his/her side.

Other detailed matters of the exemplary embodiment are included in the detailed description and the drawings.

According to the present invention, there are effects as follows.

First, it is possible to autonomously correct cervical vertebrae and induce a still point state regardless of time and place.

Second, it is possible to provide a functional pillow having functions of correcting cervical vertebrae and inducing a still point, thereby allowing a user to be naturally subjected to a treatment during sleep.

Third, it is possible to obtain a distraction effect by applying force, in different directions, to shoulders, cervical vertebrae, and the head.

The effects of the present invention are not limited to the aforementioned effects, and other effects, which are not mentioned above, will be clearly understood by those skilled in the art from the claims.

DETAILED DESCRIPTION

Figure 1:
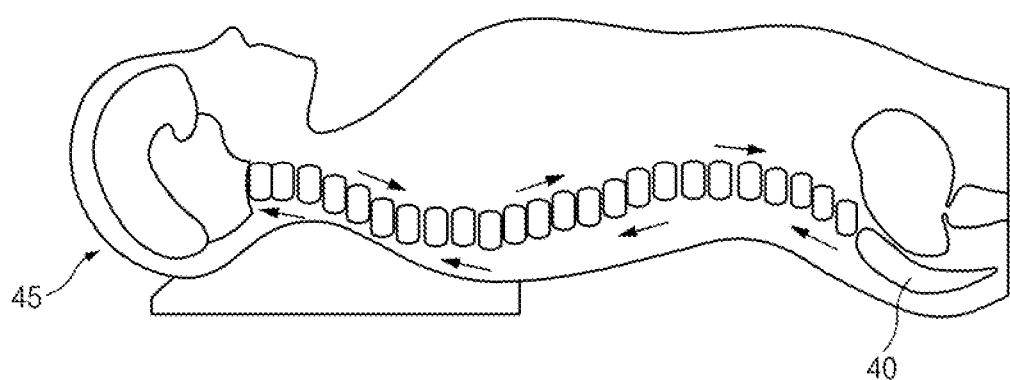
FIG. 1 is a view briefly illustrating the circulation of a cerebrospinal fluid.

Advantages and features of the present invention and methods of achieving the advantages and features will be clear with reference to exemplary embodiments described in detail below together with the accompanying drawings.

However, the present invention is not limited to the exemplary embodiments set forth below, and may be embodied in various other forms. The present exemplary embodiments are merely for rendering the disclosure of the present invention complete and are set forth to provide a complete understanding of the scope of the invention to a person with ordinary skill in the technical field to which the present invention pertains, and the present invention will only be defined by the scope of the claims. Throughout the specification, the same reference numerals denote the same constituent elements.

Hereinafter, the present invention will be described through exemplary embodiments of the present invention with reference to the drawings for explaining a functional pillow for manipulation therapy.

Figure 2A:
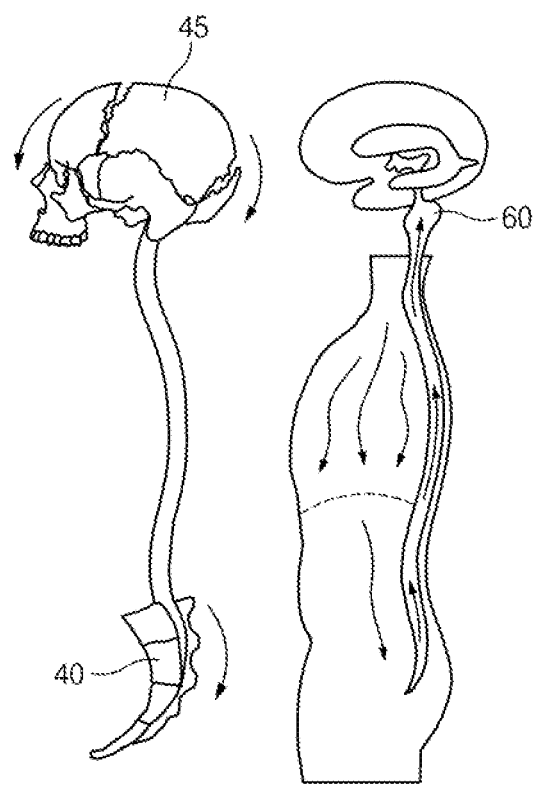
FIG. 2A is a view illustrating a flow of the cerebrospinal fluid and movements of cranial bones and lumbar vertebrae in a flexion phase.
Figure 2B:
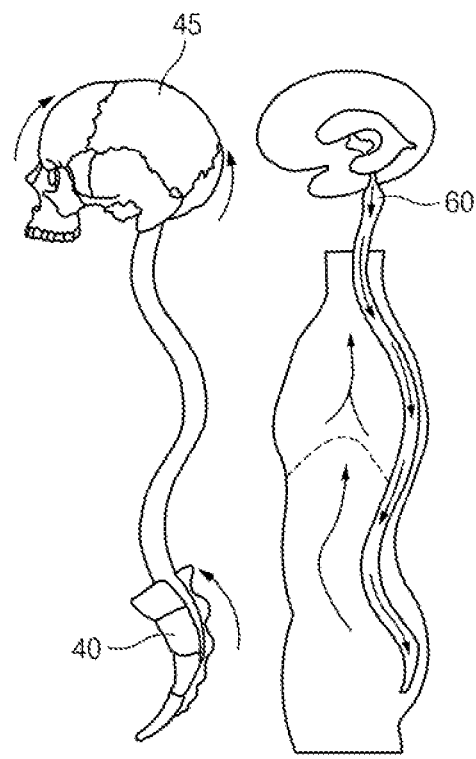
FIG. 2B is a view illustrating a flow of the cerebrospinal fluid and movements of the cranial bones and the lumbar vertebrae in an extension phase.
Figure 3A:
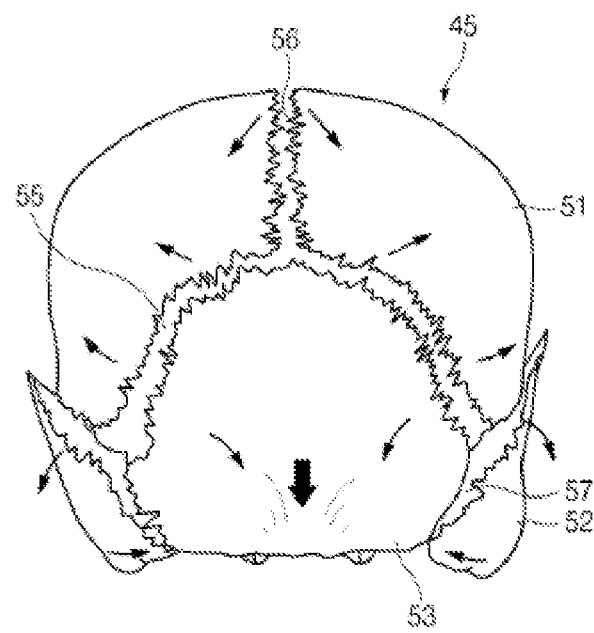
FIG. 3A is a view illustrating relaxation of an occipital region and a flow of the cerebrospinal fluid in the flexion phase.
Figure 3B:
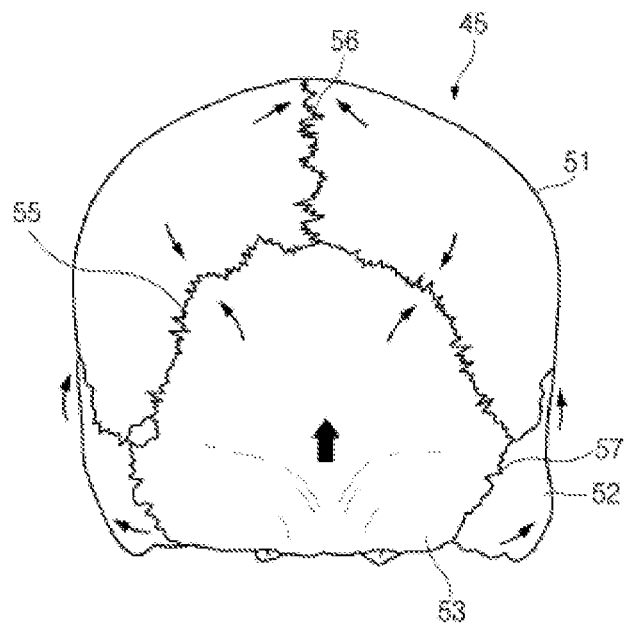
FIG. 3B is a view illustrating contraction of the occipital region and a flow of the cerebrospinal fluid in the extension phase.
Figure 4A:
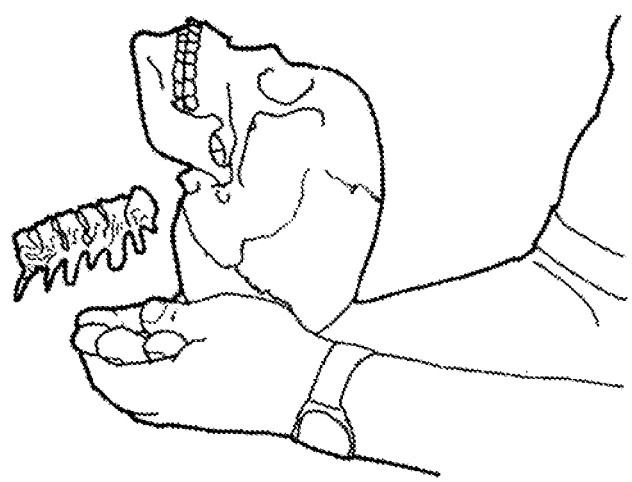
FIG. 4A is a view illustrating a procedure method of compression of the fourth ventricle CV4.
Figure 4B:
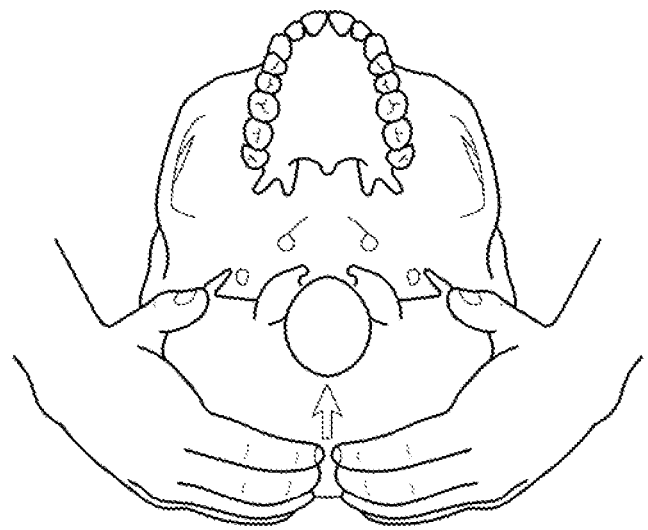
FIG. 4B is a view illustrating a procedure method of expansion of the fourth ventricle EV4.

FIG. 1 is a view briefly illustrating the circulation of a cerebrospinal fluid. FIG. 2A is a view illustrating a flow of the cerebrospinal fluid and movements of cranial bones and lumbar vertebrae in a flexion phase, and FIG. 2B is a view illustrating a flow of the cerebrospinal fluid and movements of the cranial bones and the lumbar vertebrae in an extension phase. FIG. 3A is a view illustrating relaxation of an occipital region and a flow of the cerebrospinal fluid in the flexion phase, and FIG. 3B is a view illustrating contraction of the occipital region and a flow of the cerebrospinal fluid in the extension phase. FIG. 4A is a view illustrating a procedure method of compression of the fourth ventricle CV4, and FIG. 4B is a view illustrating a procedure method of expansion of the fourth ventricle EV4.

Referring to FIGS. 1 to 4, parietal bones 51 are quadrangular and flat bones that cover a rear upper side of a neurocranium in which a brain is placed. The number of parietal bones 51 is two, and both the parietal bones 51 protrude outward. The two parietal bones 51 abut each other through a sagittal suture 56. The parietal bones 51 are connected to an occipital bone 53 through a lambdoid suture 55. Temporal bones 52 are disposed in temporal regions. The cranial bone 45 is tissue having flexibility which is contracted in the flexion phase and expanded in the extension phase. With the aforementioned structures, the cranial bones 45 may be repeatedly contracted and relaxed. A craniosacral rhythm shows information about stress or immunity. In the case of a healthy person, the flexion phase and the extension phase are cycled 8 to 12 times, such that the craniosacral movement is very stable.

The flexion means expansion or extension. The craniosacral rhythm can be sensed by hand. The feeling of the flexion transmitted to the hand can be understood as 'a feeling that a body expands' or 'a feeling that the entire body rotates outward and becomes wide', and the flexion is also called 'an external rotation'.

The extension (compression) has an opposite concept or an opposite feeling to the flexion. The extension can be understood as contraction. The extension can be understood as 'a feeling as if a body is deeply drawn'. In some instances, the extension is explained as a feeling that the entire body rotates inward and becomes narrow. The extension is also called 'an internal rotation'.

The cycle of the craniosacral movement includes two processes of the 'flexion' and the 'extension' or the 'expansion' and the 'contraction'. A point between the flexion and the extension may be called 'a neutral point'. At the neutral point, the human body feels that the human body is stopped, and the human body is in a 'relaxation' state in which tension is relaxed. The cycles of the flexion and the extension may be constant and equal to each other. If the cycles of the flexion and the extension are different from or are not coincident with each other, the human body may have abnormality.

The flexion phase and the extension phase depend on the circulation of the cerebrospinal fluid (CSF). The cerebrospinal fluid is created in a ventricle. The ventricle refers to a space placed in a brain of the human body, and the ventricle is surrounded by an ependyma. The ventricles include three types of ventricles including lateral ventricles, a third ventricle, and a fourth ventricle 60. A total of four ventricles, which include two left and right ventricles, a single third ventricle, and a single fourth ventricle 60, constitute a cerebral ventricular system.

Among the craniosacral therapies, CV4 and EV4 techniques refer to techniques of creating a still point by applying a technique to an occipital region of a user.

The compression of the fourth ventricle, that is, the CV4 technique (4th ventricular compression variation, CV-4 technique) is a method of compressing both sides of an external occipital protuberance 54 in the occipital region. The CV4 is one of the methods for promoting the creation of the still point, and refers to the compression or narrowing of the ventricle.

The CV4 technique is a method of inducing the still point by interrupting rhythm in the flexion phase, and reduces an ability of an occipital squama which has an effect on a change in pressure of the spinal cord. Therefore, pressure of the spinal cord in the cranial bones 45 is increased, and as a result, the cerebrospinal fluid is directed to all other possible routes. For this reason, the CV4 technique promotes the movement of the cerebrospinal fluid, and exchanges the cerebrospinal fluid.

The expansion of the fourth ventricle, that is, the EV4 technique (expansion of 4th ventricle) is a method of inducing the still point in the extension phase. The expansion of the fourth ventricle is a method of compressing the external occipital protuberance 54 in the occipital region. The external occipital protuberance 54 is the most protruding portion at a center of the large occipital squama that occupies a rear side of the occipital bone 53. The EV4 corresponds to the extension phase, and expands the fourth ventricle 60 in the cranial bones 45 by interrupting the protruding of the external occipital protuberance 54 by compressing the external occipital protuberance 54 by using fingers through the internal rotation.

By the compression of the fourth ventricle and/or the expansion of the fourth ventricle, the overall movement of the craniosacral system disappears, and thus the craniosacral system is in a completely stopped state. This is called a still point. The still point is created semi-compulsorily by compressing and/or expanding the fourth ventricle 60.

The craniosacral system may show the movement such as spasm, pulsation, or swaying, and when the practitioner tries to provide resistance by compressing and/or expanding the fourth ventricle 60, the activity of the craniosacral system is consequently and instantaneously stopped. In this case, the still point occurs.

During the still point process, the human body begins to be relaxed. From this point, the pains, which have occurred before, disappear slowly. Further, sacroiliac somatic dysfunction at the waist and the pelvis begins to be corrected naturally. Subsequently, the user's breathing also becomes steady, and tensed muscles begin to relax. The still point is maintained from as short as several seconds to as long as several minutes. When the still point phenomenon ends, the movement of the craniosacral system begins again. From the general observation, the amplitude of a symmetrical and increased movement is detected. The still point ends, the activity of the craniosacral system becomes better, and the movement is symmetrically restored. The still point is effective in smoothly adjusting an action of the craniosacral system.

Hereinafter, a functional pillow for manipulation therapy according to an exemplary embodiment of the present invention, which adopts the craniosacral therapy, will be described.

Based on a state in which a user lies while resting his/her head on the functional pillow for manipulation therapy and looking at a ceiling, a direction toward the user's body is defined as a front direction, a direction opposite to the front direction is defined as a rear direction, directions toward the temporal bones 52 of the user are defined as left and right directions, a direction toward the frontal bone of the user is defined as an upward direction, and a direction toward the occipital bone 53 of the user is defined as a downward direction.

Figure 5:
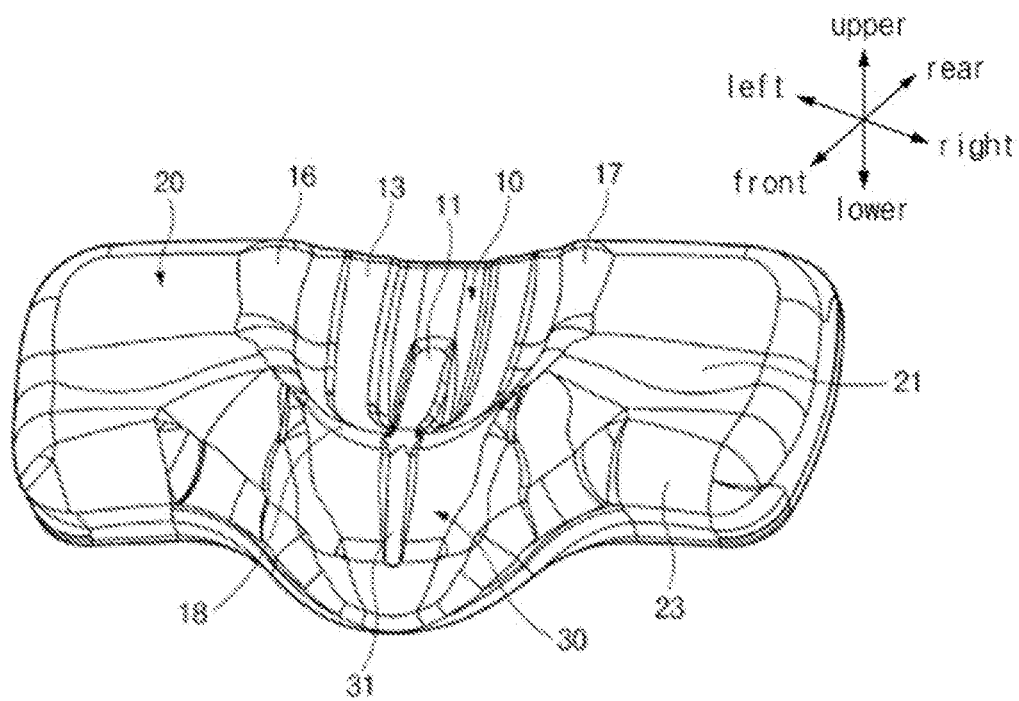
FIG. 5 is a perspective view of a functional pillow for manipulation therapy according to an exemplary embodiment of the present invention.
Figure 6:
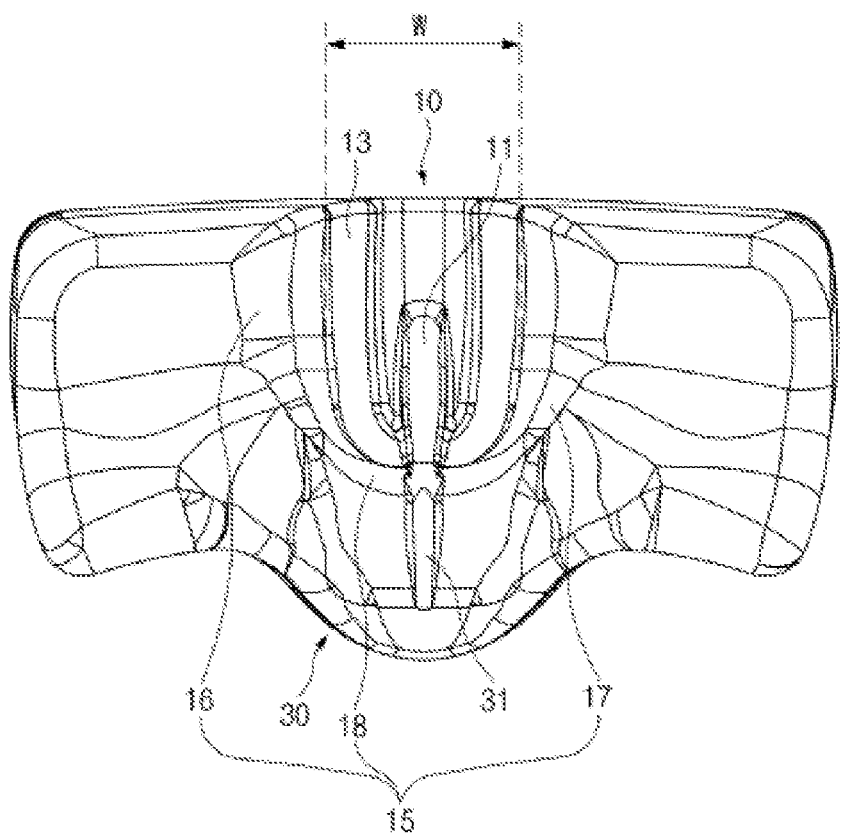
FIG. 6 is a top plan view of the functional pillow for manipulation therapy according to the exemplary embodiment of the present invention.
Figure 7:
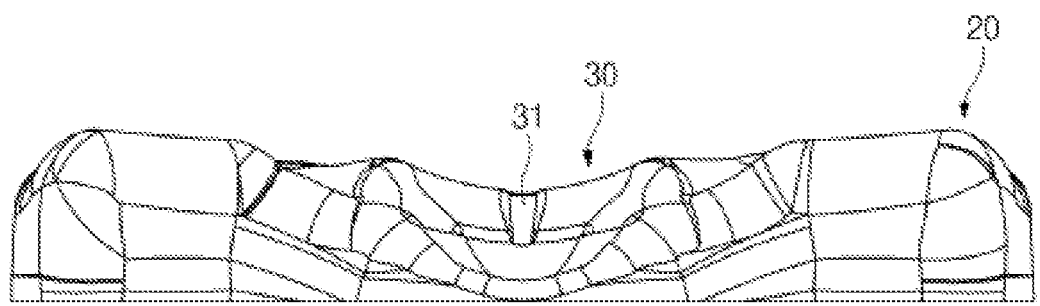
FIG. 7 is a front view of the functional pillow for manipulation therapy according to the exemplary embodiment of the present invention.
Figure 8:
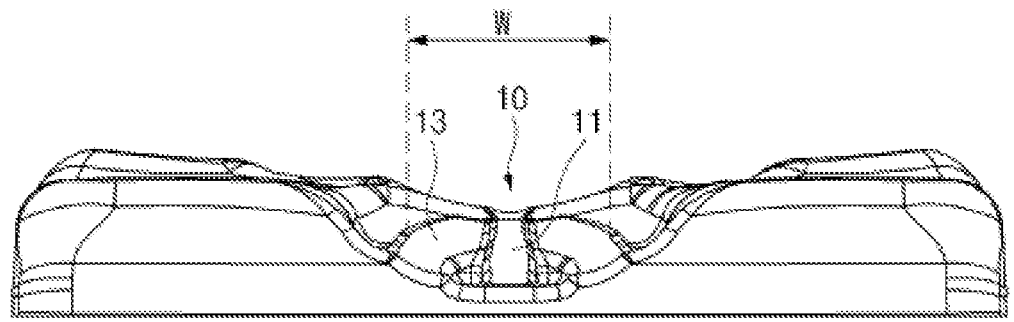
FIG. 8 is a rear view of the functional pillow for manipulation therapy according to the exemplary embodiment of the present invention.

FIG. 5 is a perspective view of the functional pillow for manipulation therapy according to the exemplary embodiment of the present invention. FIG. 6 is a top plan view of the functional pillow for manipulation therapy according to the exemplary embodiment of the present invention. FIG. 7 is a front view of the functional pillow for manipulation therapy according to the exemplary embodiment of the present invention. FIG. 8 is a rear view of the functional pillow for manipulation therapy according to the exemplary embodiment of the present invention. Referring to FIGS. 5 to 8, the functional pillow for manipulation therapy according to the exemplary embodiment of the present invention includes an occipital region accommodating portion 10 which accommodates and supports the occipital region, a cervical vertebrae support portion 30 which extends from the occipital region accommodating portion 10 and supports the cervical vertebrae, and a fourth ventricle compressing protrusion 13 which protrudes from the occipital region accommodating portion 10.

The fourth ventricle compressing protrusion 13 applies pressure to the occipital region of the user. The fourth ventricle compressing protrusion 13 induces the still point in the flexion phase.

The fourth ventricle compressing protrusion 13 may be formed in a 'V' or 'U' shape so as to stimulate left and right sides of the occipital region. The fourth ventricle compressing protrusion 13 may be formed in a horseshoe shape. The fourth ventricle compressing protrusion 13 applies pressure to both left and right surfaces of the occipital bone 53. The fourth ventricle compressing protrusion 13 may be formed at a point at a distance of 3 to 4 cm from the external occipital protuberance 54 in the left and right directions. The fourth ventricle compressing protrusion 13 compresses the user's ventricle.

The temporal bones 52 and the occipital bone 53 are connected by an occipitomastoid suture 57. The fourth ventricle compressing protrusion 13 is formed at a position that does not face the occipitomastoid suture 57. Therefore, a width W of the fourth ventricle compressing protrusion 13 in the left and right directions is less than 10 cm. The width W of the fourth ventricle compressing protrusion 13 in the left and right directions may be equal to or more than 2 cm. Otherwise, the width W of the fourth ventricle compressing protrusion 13 in the left and right directions may be equal to or greater than 2 cm or equal to or smaller than 7 cm. The restriction to the width prevents the fourth ventricle compressing protrusion 13 from stimulating the temporal bones 52.

The functional pillow for manipulation therapy according to the exemplary embodiment of the present invention includes a fourth ventricle expanding protrusion 11 which protrudes from the occipital region accommodating portion 10. A plurality of fourth ventricle compressing protrusions 13 may be formed to be elongated in the left and right directions, and the fourth ventricle expanding protrusion 11 may be formed between the plurality of fourth ventricle compressing protrusions 13.

The occipital region accommodating portion 10 is a portion which accommodates the occipital bone and has a shape recessed downward. The occipital region accommodating portion 10 supports the occipital region. The occipital region accommodating portion 10 may have a circular or semi-circular shape, and includes sidewall portions 15, to be described below, which stand to support the occipital region.

The cervical vertebrae support portion 30 supports the user's cervical vertebrae. The cervical vertebrae support portion 30 may be formed in the front and rear directions. The cervical vertebrae support portion 30 extends toward a front side of the occipital region accommodating portion 10. A height of the cervical vertebrae support portion 30 in the up and down directions may be gradually decreased as the cervical vertebrae support portion 30 extends forward.

The fourth ventricle expanding protrusion 11 applies pressure to the external occipital protuberance 54 in the user's occipital region. The fourth ventricle expanding protrusion 11 induces the still point in the extension phase. The fourth ventricle expanding protrusion 11 spreads and relaxes the cranial bones 45. The fourth ventricle expanding protrusion 11 induces pumping of the cerebrospinal fluid.

The fourth ventricle expanding protrusion 11 performs the function corresponding to the EV4 among the craniosacral therapies. A trough may be formed at a portion where the fourth ventricle compressing protrusions 13 abut the occipital region so as to increase a contact area with the occipital region. With the trough, a support area for the occipital region is increased, and as a result, the user may take a more comfortable posture. However, a shape and a position of the fourth ventricle compressing protrusion 13 may be changed because it is acceptable as long as the fourth ventricle compressing protrusion 13 is formed at a position where the fourth ventricle compressing protrusion 13 compresses the left and right sides of the external occipital protuberance 54.

The fourth ventricle compressing protrusion 13 and the fourth ventricle expanding protrusion 11 may be connected to each other. The fourth ventricle compressing protrusion 13 may be formed in a shape that surrounds the occipital region inward so as to softly compress the occipital region from the left and right sides, and the fourth ventricle expanding protrusion 11 may be connected to a center of the fourth ventricle compressing protrusion 13 and may extend into the fourth ventricle compressing protrusion 13. The fourth ventricle compressing protrusion 13 may be spaced apart from the fourth ventricle expanding protrusion 11. However, in a case in which the fourth ventricle compressing protrusion 13 and the fourth ventricle expanding protrusion 11 are connected to each other to increase a surface area of the fourth ventricle expanding protrusion 11, it is possible to allow the user to feel more comfortable by dissipating the pressure applied to the user's occipital region.

The occipital region accommodating portion 10 includes the sidewall portions 15 which define an approximately semi-circular boundary and support the occipital region. Because the occipital region accommodating portion 10 needs to be formed in a shape that surrounds the occipital region inward so as to softly compress the occipital region from the left and right sides, the occipital region accommodating portion 10 may have a groove formed therein so as to accommodate the occipital region. An edge of the occipital region accommodating portion 10 is formed by the sidewall portions 15. The sidewall portions 15 support the occipital region.

The sidewall portions 15 include a left sidewall portion 16 and a right sidewall portion 17 which support the left and right sides of the occipital region, respectively, and a cervical vertebrae connecting partition wall 18 which defines a boundary with the cervical vertebrae support portion 30. The sidewall portions 15 include the left sidewall portion 16 and the right sidewall portion 17. The left sidewall portion 16 and the right sidewall portion 17 support the temporal bones 52. The sidewall portions 15 include the cervical vertebrae connecting partition wall 18. The fourth ventricle compressing protrusion 13 is formed between the left sidewall portion 16 and the right sidewall portion 17, and the fourth ventricle expanding protrusion 11 is formed between the fourth ventricle compressing protrusions 13.

The fourth ventricle expanding protrusion 11 may extend from the cervical vertebrae connecting partition wall 18. The fourth ventricle expanding protrusion 11 may extend rearward from the cervical vertebrae connecting partition wall 18. The fourth ventricle expanding protrusion 11 may be formed to be spaced apart from the cervical vertebrae connecting partition wall 18. However, because there is concern that sound sleep may be hindered in a case in which the user receives excessive pressure from the fourth ventricle expanding protrusion 11, a contact area between the fourth ventricle expanding protrusion 11 and the occipital region may be maintained to be equal to or larger than a predetermined area. Therefore, the cervical vertebrae connecting partition wall 18 and the fourth ventricle expanding protrusion 11 may be connected to each other.

The functional pillow for manipulation therapy according to the exemplary embodiment of the present invention includes lateral support portions 20 which extend from the sidewall portions 15 in the left and right directions. The lateral support portions 20 may be formed at left and right sides of the occipital region accommodating portion 10, respectively. When the user lies on his/her side while looking at the left or right side, the lateral support portion 20 supports the temporal bone 52. The lateral support portions 20 are defined from the left sidewall portion 16 and the right sidewall portion 17. The lateral support portions 20 are formed to have a predetermined height or greater because a diameter of the user's cranial bones 45 and the user's chest circumference vary when the user lies on his/her side. That is, a height of the lateral support portion 20 is determined such that the user's cervical vertebrae are maintained in a straight shape if possible.

The lateral support portion 20 may have an ear accommodating groove 21 which is recessed to accommodate the user's ear. The ear accommodating groove 21 is formed to be lower than a general height of the lateral support portion 20. Because the user's ear protrudes in a lateral direction, a load of the head is applied to one ear of the user when the user lies on his/her side. Therefore, as the ear is positioned in the ear accommodating groove 21, a load of the head may be uniformly applied to the temporal bone 52, the parietal bone 51, and the frontal bone.

The occipital region accommodating portion 10 may have a spinous process accommodating groove 31 which accommodates spinous processes of the cervical vertebrae. The spinous process accommodating groove 31 may be formed to be elongated in the front and rear directions. The spinous processes are formed to protrude from the cervical vertebrae. Therefore, a load may be concentrated at the spinous processes. The occipital region accommodating portion 10 has the spinous process accommodating groove 31 in order to reduce the load concentrated at the spinous processes. Since the spinous processes are inserted into the spinous process accommodating groove 31, a contact area is increased, and more uniform pressure is applied on the cervical vertebrae.

The fourth ventricle expanding protrusion 11 may be formed in a longitudinal direction of the spinous process accommodating groove 31. The fourth ventricle expanding protrusion 11 and the spinous process accommodating groove 31 are formed in a straight line. The occipital protuberance may be formed in a center line of the cranial bones 45, and the cervical vertebrae may be formed straight in a center line of the body. A height of the fourth ventricle expanding protrusion 11 is gradually increased toward the cervical vertebrae connecting partition wall 18, and a height of the spinous process accommodating groove 31 is gradually decreased forward from the cervical vertebrae connecting partition wall 18.

Figure 9:
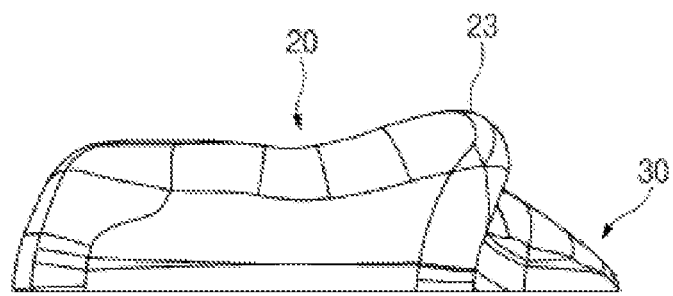
FIG. 9 is a side view of the functional pillow for the manipulation therapy according to the exemplary embodiment of the present invention.

FIG. 9 is a side view of the functional pillow for the manipulation therapy according to the exemplary embodiment of the present invention.

Referring to FIG. 9, the lateral support portion 20 has a crest 23 which extends in an elongated manner so as to support lateral sides of the user's cervical vertebrae. The lateral support portion 20 has the crest 23. The crest 23 may protrude to be highest in the lateral support portion 20. The crest 23 may be formed to be inclined so as not to interfere with the user's jaws. Because a diameter of the neck is smaller than the diameter of the cranial bones 45, the neck is not supported when the user lies on his/her side. Therefore, the crest 23 protrudes from the front side of the lateral support portion 20 in the lateral direction, and may support the user's neck. All of the user's temporal bone 52 and the lateral sides of the cervical vertebrae are supported, and as a result, a more comfortable posture may be maintained.

Figure 10A:
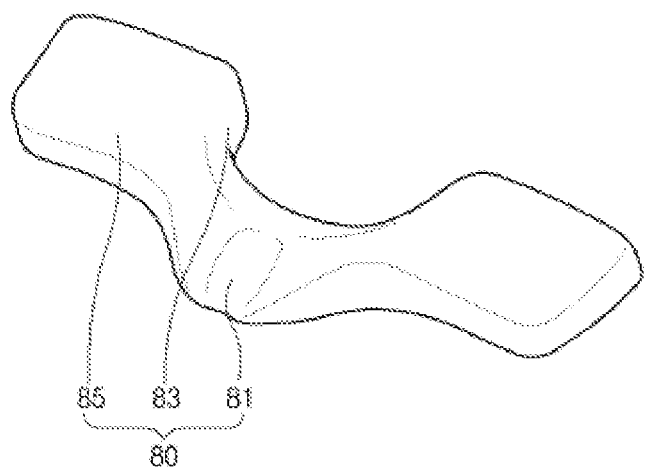
FIG. 10A is a perspective view of a core portion according to the exemplary embodiment of the present invention.
Figure 10B:
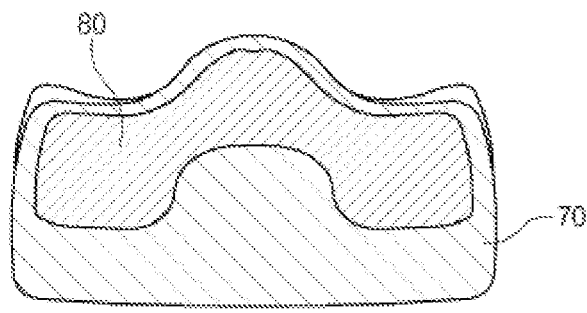
FIG. 10B is a bottom plan view of the functional pillow for manipulation therapy to which the core portion is attached.
Figure 10C:
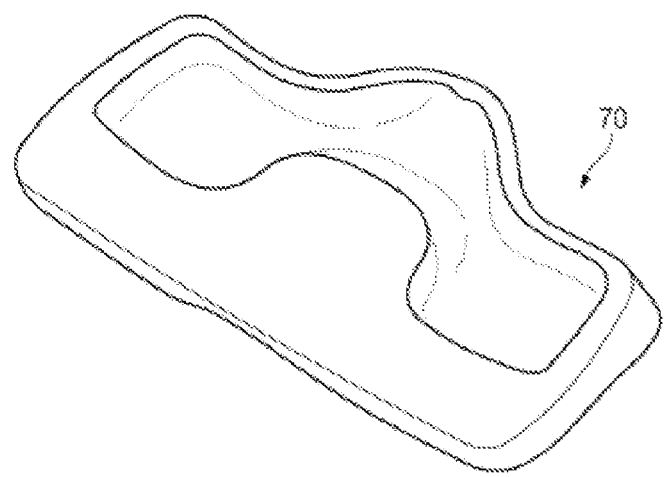
FIG. 10C is a view illustrating an appearance of an external shape forming portion having no core portion.

FIG. 10 is a view illustrating a core portion and an external shape forming portion according to the exemplary embodiment of the present invention, in which FIG. 10A is a perspective view of the core portion according to the exemplary embodiment of the present invention, FIG. 10B is a bottom plan view of the functional pillow for manipulation therapy to which the core portion is attached, and FIG. 10C is a view illustrating an appearance of the external shape forming portion having no core portion.

Referring to FIG. 10, the functional pillow for manipulation therapy according to the exemplary embodiment of the present invention includes a core portion 80 which includes a cervical vertebrae support core 81 for supporting a load applied from the cervical vertebrae and occipital region fixing cores 83 for fixing and supporting an edge of the occipital bone 53, and an external shape forming portion 70 which surrounds an upper surface of the core portion 80, is made of foam having lower hardness than the core portion 80, and has a protrusion that applies pressure to the occipital bone 53 at a position where the occipital bone 53 is not supported by the occipital region fixing cores 83.

The occipital region accommodating portion 10 and the cervical vertebrae support portion 30 may be made of foam. The external shape forming portion 70 is a portion which comes into direct contact with the user's occipital region and cervical vertebrae, and the external shape forming portion 70 uniformly absorbs pressure by being deformed in accordance with a load applied from the user. The external shape forming portion 70 is made of foam having lower hardness than the core portion 80. The core portion 80 is made of foam having physical properties different from those of the external shape forming portion 70. The core portion 80 may have higher hardness than the external shape forming portion 70. The foam has elastic force, but durability of the elasticity may be degraded because moisture is discharged over time. The core portion 80 supports a load of the external shape forming portion 70, thereby increasing durability. The core portion 80 supports the external shape forming portion 70, and prevents the external shape forming portion 70 from being excessively deformed due to durability that may deteriorate because of the user's weight over a long period of time.

The external shape forming portion 70 has the protrusion. The protrusion may be the fourth ventricle expanding protrusion 11 and the fourth ventricle compressing protrusion 13. The core portion 80 may not support a load applied to the fourth ventricle expanding protrusion 11 and the fourth ventricle compressing protrusion 13. The fourth ventricle expanding protrusion 11 and the fourth ventricle compressing protrusion 13 may be more freely deformed, and as a result, the pressure applied to the user's occipital bone 54 is reduced. Therefore, the user may sleep deeply even though the user uses the functional pillow for manipulation therapy over a long period of time.

The functional pillow for manipulation therapy according to the exemplary embodiment of the present invention includes the external shape forming portion 70 which has the occipital region accommodating portion 10, the cervical vertebrae support portion 30, the fourth ventricle expanding protrusion 11, and/or the fourth ventricle compressing protrusion 13, and the core portion 80 which is disposed inside the external shape forming portion 70 and have hardness different from that of the external shape forming portion 70. The external shape forming portion 70 and the core portion 80 have different hardness. In particular, the hardness of the core portion 80 is higher than the hardness of the external shape forming portion 70.

The core portion 80 includes the cervical vertebrae support core 81 which is formed at a lower side of the cervical vertebrae support portion 30, and the occipital region fixing cores 83 which are formed at a lower side of an edge of the occipital region accommodating portion 10 so as to avoid lower sides of the fourth ventricle expanding protrusion 11 and the fourth ventricle compressing protrusion 13. The cervical vertebrae support core 81 supports the cervical vertebrae, and restricts shape deformation of the cervical vertebrae support portion 30. However, since the core portion 80 is formed at the edge of the occipital region accommodating portion 10, the core portion 80 does not restrict the deformation of the occipital region accommodating portion 10. Therefore, the relaxation of the user's neck muscle is not restricted.

The external shape forming portion 70 further includes the lateral support portions 20 which extend in the left and right directions of the occipital region accommodating portion 10, and the core portion 80 includes lateral support cores 85 which extend from the occipital region fixing cores 83 and are formed at the lower sides of the lateral support portions 20.

The lateral support core 85 inhibits the lateral support portion 20 from being deformed. The user may lie on his/her side during sleep. In this case, if a degree to which the lateral support portion 20 is deformed is large, the cervical vertebrae are not maintained in a straight shape, but may be inclined. The lateral support core 85 restricts the deformation of the lateral support portion 20 so as to allow the cervical vertebrae to be maintained in a straight shape.

Figure 11A:
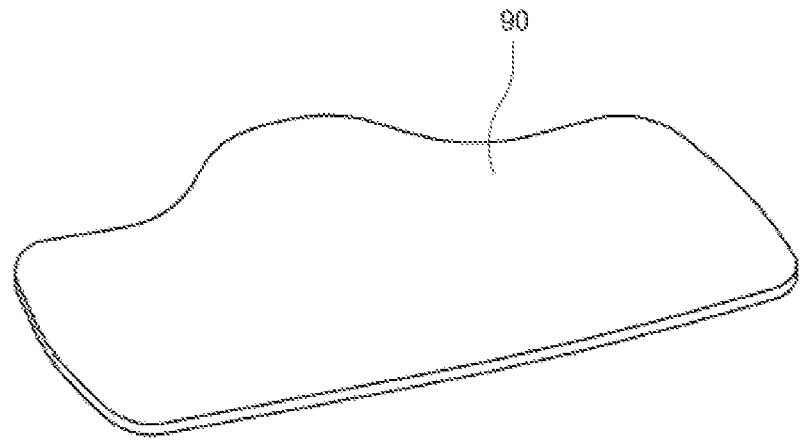
FIG. 11A is a view illustrating a pad according to the exemplary embodiment of the present invention.
Figure 11B:
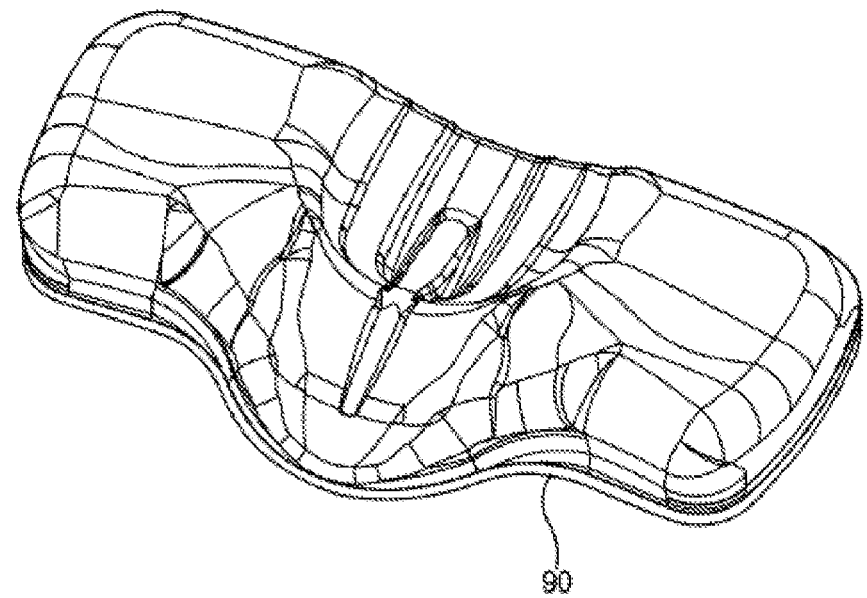
FIG. 11B is a perspective view of the functional pillow for manipulation therapy to which the pad is attached.

FIG. 11A is a view illustrating a pad according to the exemplary embodiment of the present invention, and FIG. 11B is a perspective view of the functional pillow for manipulation therapy to which the pad is attached.

Referring to FIGS. 11A to 11B, the functional pillow for manipulation therapy according to the exemplary embodiment of the present invention further includes a pad 90 which is disposed at the lower sides of the external shape forming portion 70 and the core portion 80 and increases a height of the external shape forming portion 70. Based on the user's body size, a plurality of pads 90 may be used or the pad 90 may be removed.

The foam has a plurality of fine holes formed in a surface thereof, and thus has a high frictional coefficient. Therefore, even though no separate attachment member is provided, it is possible to maintain a state in which the pad 90 is attached to the functional pillow for manipulation therapy. In particular, an outer sheath of the functional pillow for manipulation therapy is formed to surround both of the pad 90 and the functional pillow for manipulation therapy. Therefore, the functional pillow for manipulation therapy may be integrated without a separate adhesive member or the like, thereby improving the user's convenience.

Figure 12:
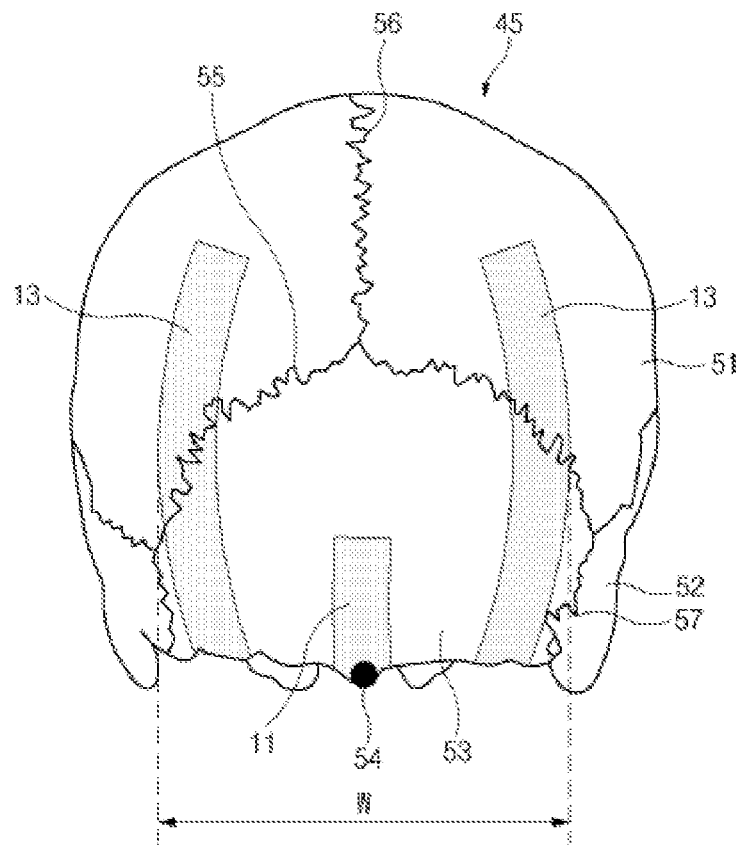
FIG. 12 is a view illustrating a compressing point of the functional pillow for manipulation therapy according to the exemplary embodiment of the present invention.

FIG. 12 is a view illustrating a compressing point of the functional pillow for manipulation therapy according to the exemplary embodiment of the present invention.

Referring to FIGS. 5 and 12, the functional pillow for manipulation therapy according to the exemplary embodiment of the present invention includes the fourth ventricle compressing protrusion 13 which applies pressure to the occipital bone 53, the fourth ventricle expanding protrusion 11 which applies pressure to the external occipital protuberance 54, and the occipital region accommodating portion 10 which is formed with the fourth ventricle expanding protrusion 11 and the fourth ventricle compressing protrusion 13 and recessed to fixedly support the occipital region.

In addition, the functional pillow for manipulation therapy according to the exemplary embodiment of the present invention includes the fourth ventricle compressing protrusion 13 which induces the flexion phase of the cranial bone 45, the fourth ventricle expanding protrusion 11 which induces the extension phase of the cranial bones 45, and the occipital region accommodating portion 10 which fixedly supports the occipital region, and is formed with the fourth ventricle compressing protrusion 13 and the fourth ventricle expanding protrusion 11 at a surface facing the occipital bone 53.

The functional pillow for manipulation therapy according to the exemplary embodiment of the present invention includes the fourth ventricle compressing protrusion 13 which inhibits the left and right sides of the occipital bone 53 from further expanding in the flexion phase in which the left and right sides of the occipital bone 53 expand when the cerebrospinal fluid is created in the flexion phase, the fourth ventricle expanding protrusion 11 which inhibits the external occipital protuberance 54 of the occipital bone 53 from further protruding in the extension phase in which the external occipital protuberance 54 of the occipital bone 53 protrudes when the creation of the cerebrospinal fluid is stopped in the extension phase, and the occipital region accommodating portion 10 which fixedly supports the occipital region, and is formed with the fourth ventricle compressing protrusion 13 and the fourth ventricle expanding protrusion 11 at a surface facing the occipital bone 53.

The fourth ventricle compressing protrusion 13 applies pressure to the occipital bone 53, and the fourth ventricle expanding protrusion 11 applies pressure to the external occipital protuberance 54. In addition, the occipital region accommodating portion 10 fixedly supports the occipital region. Therefore, the user is subjected to the craniosacral therapy during sound sleep. In addition, there is an effect in that the user is simultaneously subjected to the CV4 and the EV4 of the craniosacral therapies, and as a result, it is possible to more frequently induce the still point state.

Therefore, in a case in which the functional pillow for manipulation therapy according to the exemplary embodiment of the present invention is used, the functional pillow for manipulation therapy affects an activity of a diaphragm and an autonomic nerve adjustment for respiration, thereby relaxing tonus of a sympathetic nervous system. In addition, since the CV4 (the compression of the fourth ventricle) technique and the EV4 (the expansion of the fourth ventricle) technique relax all connective tissues of the human body, the CV4 technique and the EV4 technique have effects of relaxing chronic stress strain of the sympathetic nervous system of the patient, and reducing headache, strain of muscles in a rear cervical region, stiffness of a rear neck, shoulder muscle pain, fever, acute and chronic musculoskeletal diseases, low back pain, degenerative arthritis, cerebral congestion, pulmonary congestion, and edema. In addition, the CV4 technique and the EV4 technique show efficacies in respect to autism, children's distractibility, headache, low back pain, depressive disorder, and incurable diseases.

In addition, the functional pillow for manipulation therapy may be used during sleep at home, and as a result, it is possible to reduce a time-related burden of busy modern persons. In addition, the user may be autonomously subjected to the procedure without assistance of a practitioner at home, and as a result, spatial restriction and a burden of expense are reduced. In addition, since the craniosacral therapy is a therapy that induces a change of the body by very minute touch of the hands, and as a result, the craniosacral therapy does not cause an adverse effect. For this reason, the craniosacral therapy is useful not only to pregnant women or old or weak persons, but also to modern people who suffer from stress and need comfort for mind and body, spiritual comfort, and a comfortable life.

The fourth ventricle expanding protrusion 11 may be formed at a position where the fourth ventricle expanding protrusion 11 applies pressure to the external occipital protuberance 54. The fourth ventricle expanding protrusion 11 compresses the external occipital protuberance 54. The fourth ventricle expanding protrusion 11 expands the user's ventricle. The fourth ventricle expanding protrusion 11 performs the function corresponding to the EV4 among the craniosacral therapies. The fourth ventricle expanding protrusion 11 expands the fourth ventricle 60.

Figure 13:
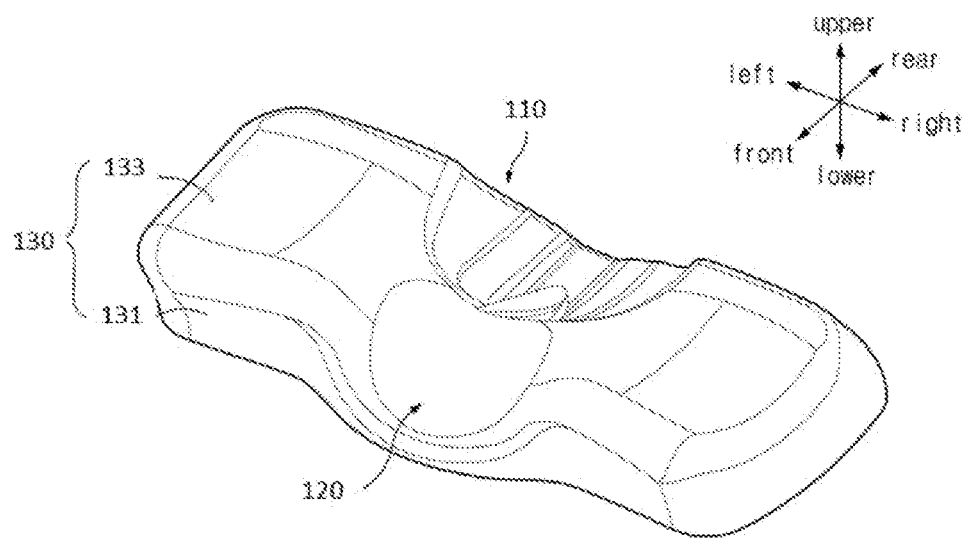
FIG. 13 is a perspective view of a functional pillow for manipulation therapy according to another exemplary embodiment of the present invention.
Figure 14:
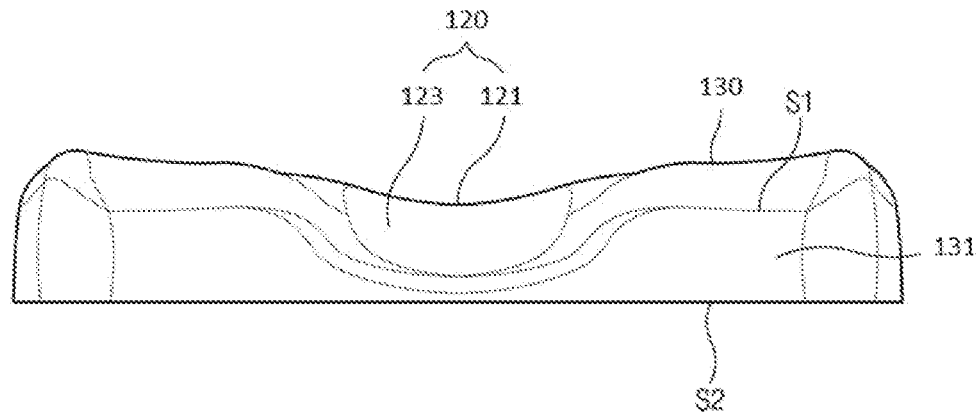
FIG. 14 is a front view of the functional pillow for manipulation therapy according to another exemplary embodiment of the present invention.
Figure 15:
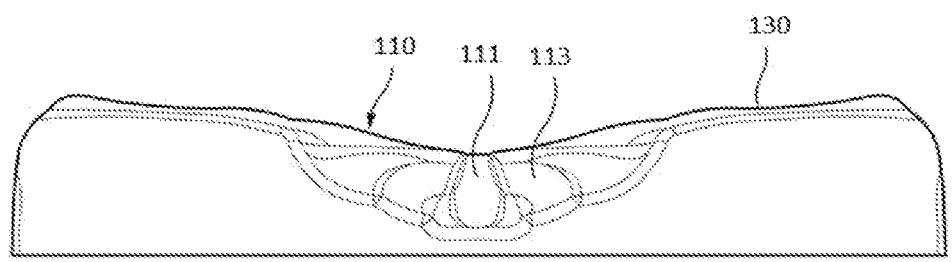
FIG. 15 is a rear view of the functional pillow for manipulation therapy according to another exemplary embodiment of the present invention.

FIG. 13 is a perspective view of a functional pillow for manipulation therapy according to another exemplary embodiment of the present invention. FIG. 14 is a front view of the functional pillow for manipulation therapy according to another exemplary embodiment of the present invention. FIG. 15 is a rear view of the functional pillow for manipulation therapy according to another exemplary embodiment of the present invention.

Referring to FIGS. 13 to 15, the functional pillow for manipulation therapy according to another exemplary embodiment of the present invention includes an occipital region accommodating portion 110 which accommodates and supports the occipital region, a cervical vertebrae support portion 120 which is formed to be inclined and supports the cervical vertebrae, and lateral support portions 130 which are formed at left and right sides of the cervical vertebrae support portion 120 and the occipital region accommodating portion 110, respectively, and support the user's head when the user lies on his/her side.

The occipital region accommodating portion 110 has a concavely recessed shape. The occipital region accommodating portion 110 accommodates the user's occipital region. The cervical vertebrae support portion 120 allows the user's cervical vertebrae to be maintained in an appropriate posture. The cervical vertebrae support portion 120 is formed to be appropriately inclined, and supports the cervical vertebrae.

The lateral support portions 130 are formed at the left and right sides of the cervical vertebrae support portion 120 and the occipital region accommodating portion 110. The user may often change his/her posture during sleep. The cervical vertebrae support portion 120 and the occipital region accommodating portion 110 support the cervical vertebrae and the occipital region while the user sleeps in an appropriate posture. The lateral support portions 130 support the parietal bone 51 and the temporal bones 52 (hereinafter, referred to as a 'temporal region') of the user when the user lies on his/her side.

The cervical vertebrae support portion 120 is inclined rearward so that a height of the cervical vertebrae support portion 120 is increased in a direction from the user's lower cervical vertebra to the user's upper cervical vertebra, and the lateral support portions 130 have shoulder pressing surfaces 131 which are inclined forward at a portion facing the user's shoulder.

The cervical vertebrae support portion 120 is formed to be inclined such that the user's upper cervical vertebra is positioned to be higher than the lower cervical vertebra when the user lies. The lateral support portion 130 has the shoulder pressing surface 131. The lateral support portion 130 is formed to be inclined so that the user's shoulder receives force toward the ground surface.

Figure 16A:
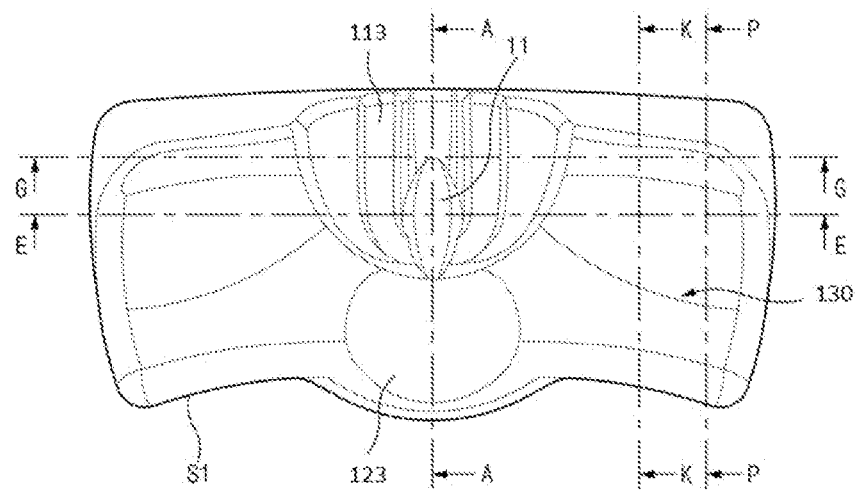
FIG. 16A is a top plan view of the functional pillow for manipulation therapy according to another exemplary embodiment of the present invention.
Figure 16B:
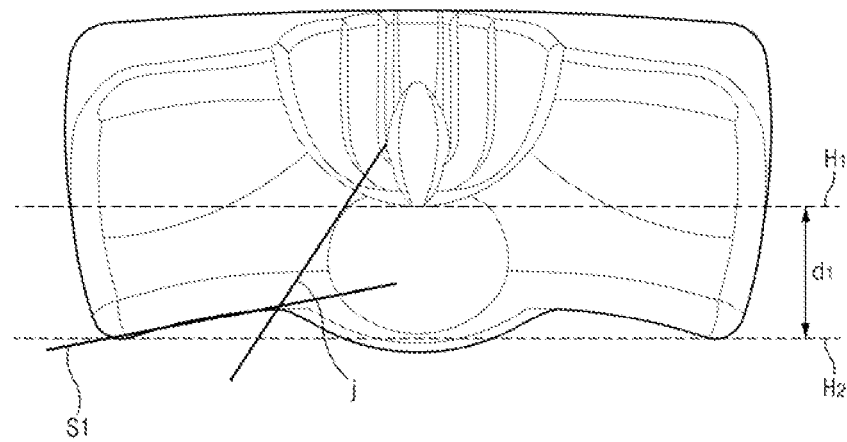
FIG. 16B is a view illustrating crests and imaginary horizontal lines in FIG. 16A.
Figure 17A:
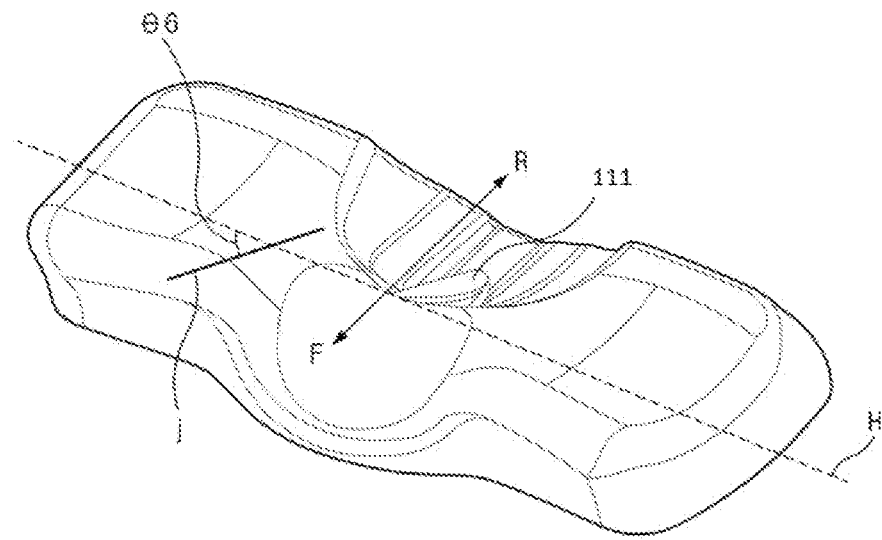
FIGS. 17A to 17C are views detailedly illustrating a shape of the functional pillow for manipulation therapy according to another exemplary embodiment of the present invention.
Figure 17B:
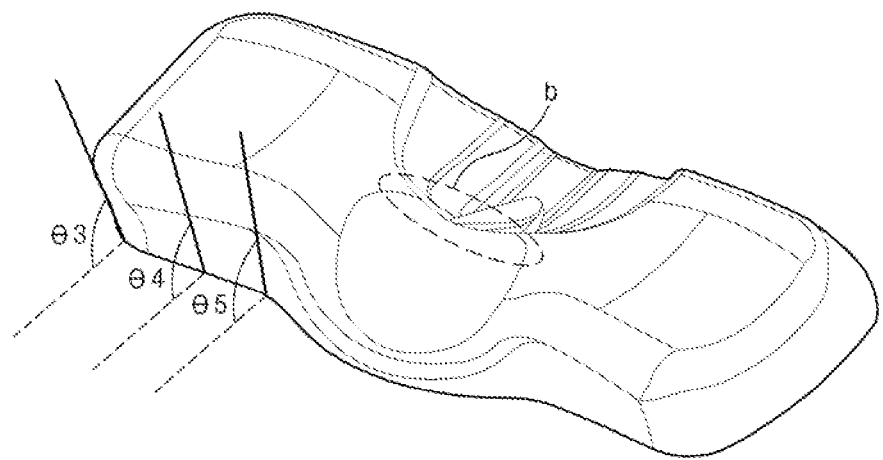
Figure 17C:
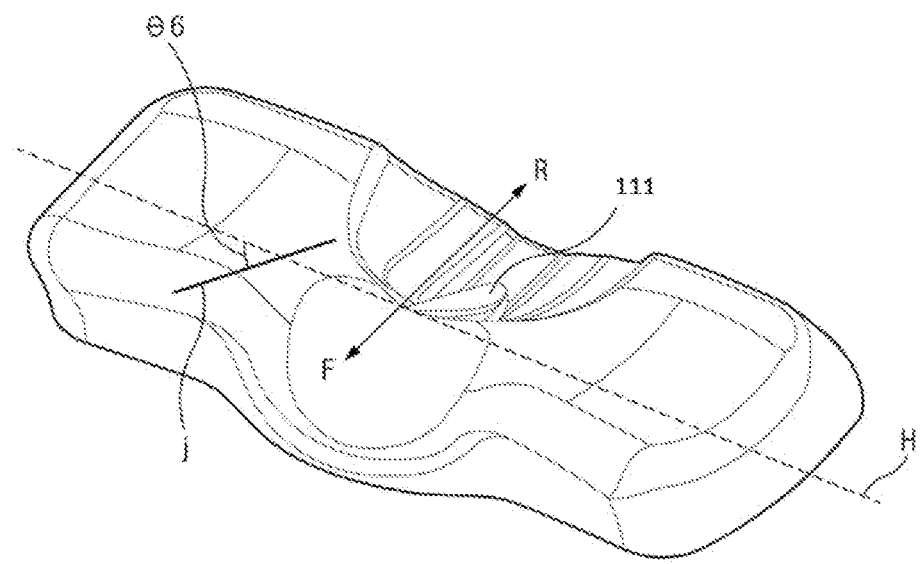

FIG. 16A is a top plan view of the functional pillow for manipulation therapy according to another exemplary embodiment of the present invention. FIG. 16B is a view illustrating crests and imaginary horizontal lines H in FIG. 16A. FIGS. 17A to 17C are views detailedly illustrating a shape of the functional pillow for manipulation therapy according to another exemplary embodiment of the present invention.

Referring to FIGS. 16A to 17C, the shoulder pressing surfaces 131 extend from the cervical vertebrae support portion 120 in the left and right directions, and a gradient with respect to a horizontal surface is gradually decreased in a direction away from the cervical vertebrae support portion 120. The gradients $\Theta 3$, $\Theta 4$, and $\Theta 5$ of the shoulder pressing surface 131 may be between 90 degrees and 75 degrees.

The gradient of the shoulder pressing surface 131 is decreased in a direction away from the user's cervical vertebrae. As an example, the gradient $\Theta 5$ of the shoulder pressing surface 131 at a portion close to the user's neck may be 89 to 90 degrees, and the gradient $\Theta 3$ at an end of the user's shoulder is decreased to about 75 degrees.

A fourth ventricle expanding protrusion 111 extends from the cervical vertebrae support portion 120, and a width d1 between a first horizontal line H1 that meets a start point of the fourth ventricle expanding protrusion 111 and a second horizontal line H2 that abuts an upper end line S1 of the shoulder pressing surface 131, among a plurality of horizontal lines H perpendicular to the longitudinal direction of the fourth ventricle expanding protrusion 111, may be between 80 millimeters and 120 millimeters.

The upper end line S1 of the shoulder pressing surface 131 may be a point where a direction of the inclination is changed from a front side to a rear side. A lower end line S2 of the shoulder pressing surface 131 may be a portion that defines a boundary with the ground surface.

If a distance between the first horizontal line H1 and the second horizontal line H2 is too short, the main function of the lateral support portion 130, which supports the temporal region, deteriorates. In addition, if a distance between the first horizontal line H1 and the second horizontal line H2 is too long, the shoulder is positioned much forward, such that the upper cervical vertebra cannot be positioned on an occipital underlying crest b. In addition, the fourth ventricle expanding protrusion 111 may also not sufficiently stimulate the external occipital protuberance 54. However, because the shoulder is inclined to gradually become lower in a direction from the neck portion to the end of the shoulder, an error may occur to a certain degree between the first horizontal line H1 and the second horizontal line H2. The fourth ventricle expanding protrusion 111 will be described in detail below.

The fourth ventricle expanding protrusion 111 extends from the cervical vertebrae support portion 120, and angles Θ1 and Θ2 between the shoulder pressing surface 131 and any one of the plurality of horizontal lines H perpendicular to the longitudinal direction of the fourth ventricle expanding protrusion 111 are gradually increased in a direction from the lower end line S2 of the shoulder pressing surface 131 to the upper end line S1 of the shoulder pressing surface 131.

With the aforementioned shape, the user's shoulder may be pressed forward and toward the ground surface. Therefore, the shoulder is fixed, and as a result, a correction effect occurs due to distraction of the cervical vertebrae.

An angle between the lower end line S2 of the shoulder pressing surface 131 and the horizontal line H may be 1 to 7 degrees, and an angle between the upper end line S1 of the shoulder pressing surface 131 and the first horizontal line H1 may be 8 to 15 degrees.

With the aforementioned shape, it is possible to reduce interference with respect to the user's jaws. In particular, it is possible to avoid interference with the shoulder when the user changes his/her posture during sleep. Therefore, a natural change in posture is not hindered, and as a result, disturbed sleep is reduced. In addition, the aforementioned shape may simultaneously perform the function of fixing the shoulder.

The cervical vertebrae support portion 120 has a cervical vertebrae accommodating groove 123 which accommodates the user's cervical vertebrae, and a lower jaw support crest j is formed to define a boundary between the cervical vertebrae accommodating groove 123 and the lateral support portion 130.

The cervical vertebrae accommodating groove 123 has a gradual valley shape, and supports the user's cervical vertebrae. The occipital underlying crest b is formed at an upper end portion of the cervical vertebrae accommodating groove 123, and the occipital region accommodating portion 110 is positioned over the occipital underlying crest b. Based on the occipital underlying crest b, the cervical vertebrae accommodating groove 123 is formed at a front side, and the fourth ventricle expanding protrusion 111 is formed at a rear side.

The lower jaw support crest j is formed on the lateral support portion 130. The lateral support portion 130 is a relatively protruding crest due to the ear accommodating groove recessed to accommodate the user's ear. The lower jaw support crest j is formed to be inclined based on the first horizontal line H1.

The functional pillow for manipulation therapy according to another exemplary embodiment of the present invention includes the fourth ventricle expanding protrusion 111 which extends from the cervical vertebrae support portion 120, protrudes from the occipital region accommodating portion 110, and inclines in a direction opposite to the direction in which the cervical vertebrae support portion 120 is inclined, and an angle Θ6 between the lower jaw support crest j and any one of the plurality of horizontal lines H perpendicular to the longitudinal direction of the fourth ventricle expanding protrusion 111 may be 40 to 65 degrees.

With the angle, no interference is caused by the shape of the functional pillow for manipulation therapy even though the user lies on his/her side during sleep in an appropriate posture. That is, there are effects of preventing interference between the shoulder and the shoulder pressing surface 131, stably supporting the jaws protruding forward, preventing excessive compression of the ear caused by the shape of the ear accommodating groove, and preventing interference between the neck and the lateral support portion 130 while the user changes his/her posture.

Figure 18:
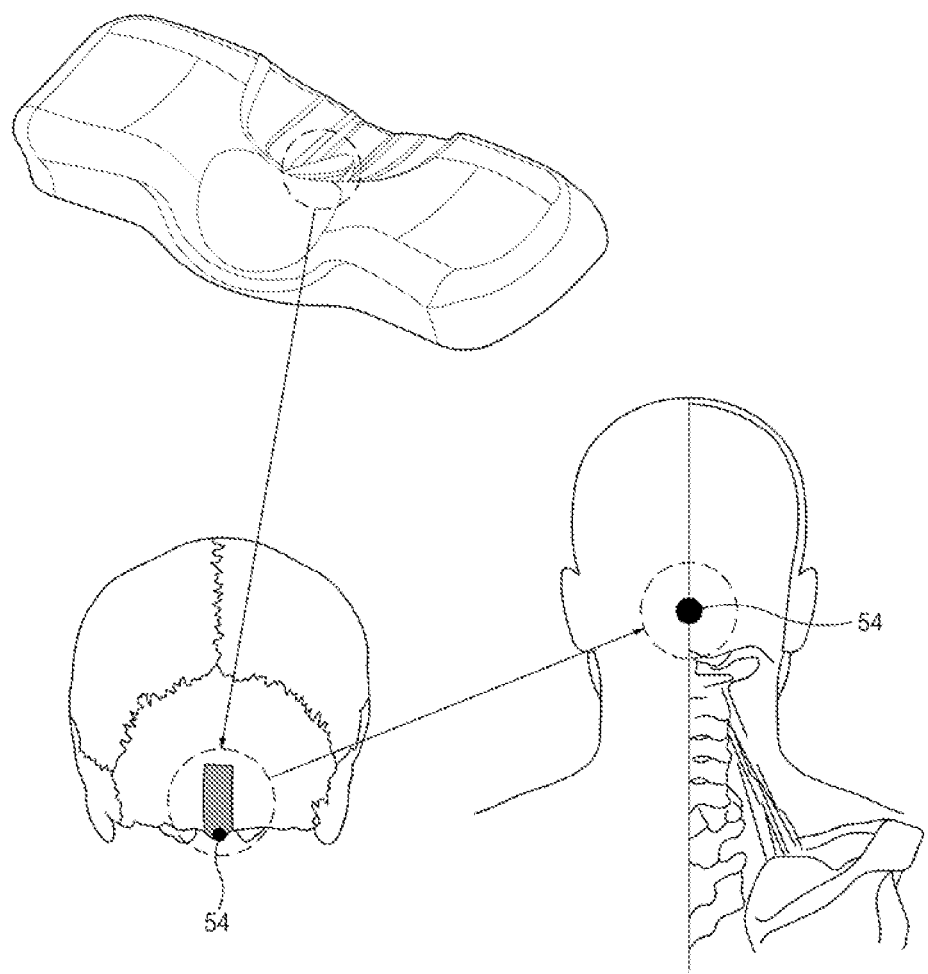
FIG. 18 is a view illustrating a stimulation point of a fourth ventricle expanding protrusion of the functional pillow for manipulation therapy according to another exemplary embodiment of the present invention.
Figure 19:
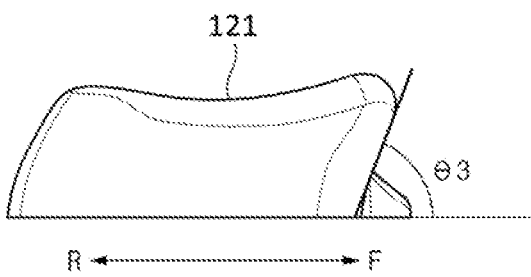
FIG. 19 is a side view of the functional pillow for manipulation therapy according to another exemplary embodiment of the present invention.
Figure 20:
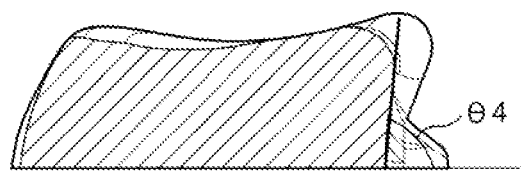
FIG. 20 is a cross-sectional view taken along line A-A of FIG. 16A.
Figure 21:
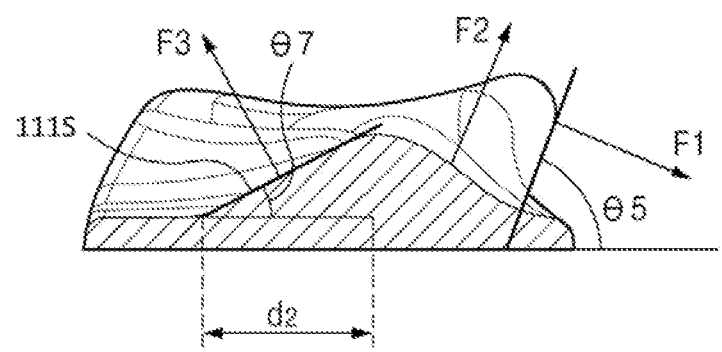
FIG. 21 is a cross-sectional view taken along line K-K of FIG. 16A.
Figure 22:
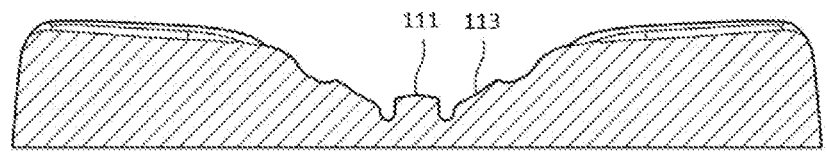
FIG. 22 is a cross-sectional view taken along line E-E of FIG. 16A.
Figure 23:
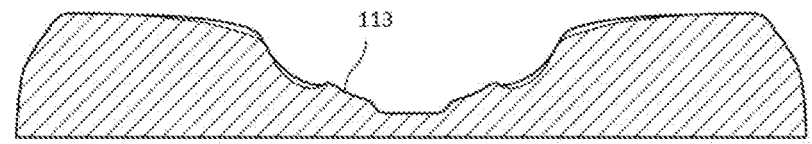
FIG. 23 is a cross-sectional view taken along line G-G of FIG. 16A.

FIG. 18 is a view illustrating a stimulation point of a fourth ventricle expanding protrusion 111 of the functional pillow for manipulation therapy according to another exemplary embodiment of the present invention. FIG. 19 is a side view of the functional pillow for manipulation therapy according to another exemplary embodiment of the present invention. FIG. 20 is a cross-sectional view taken along line A-A of FIG. 16A. FIG. 21 is a cross-sectional view taken along line K-K of FIG. 16A. FIG. 22 is a cross-sectional view taken along line E-E of FIG. 16A. FIG. 23 is a cross-sectional view taken along line G-G of FIG. 16A.

Referring to FIGS. 18 to 23, the functional pillow for manipulation therapy according to another exemplary embodiment of the present invention includes the fourth ventricle expanding protrusion 111 which protrudes from the occipital region accommodating portion 110, and inclines in a direction opposite to the direction in which the cervical vertebrae support portion 120 is inclined.

The occipital region accommodating portion 110 may have a plurality of crests and a plurality of troughs. Some of the plurality of crests are the fourth ventricle expanding protrusions 111, and other crests are the fourth ventricle compressing protrusions 113.

The fourth ventricle compressing protrusion 113 is formed on the occipital region accommodating portion 110. The fourth ventricle compressing protrusion 113 interrupts the flexion phase by stimulating the left and right sides of the occipital bone. The fourth ventricle compressing protrusion 113 implements the compression of the fourth ventricle.

The fourth ventricle expanding protrusion 111 is formed on the occipital region accommodating portion 110. The fourth ventricle expanding protrusion 111 stimulates the user's external occipital protuberance. The fourth ventricle expanding protrusion 111 is formed at a point corresponding to the user's external occipital protuberance.

The fourth ventricle expanding protrusion 111 interrupts the extension phase. The fourth ventricle expanding protrusion 111 implements the expansion of the fourth ventricle.

The fourth ventricle expanding protrusion 111 is formed to be inclined, and the inclination is decreased in a direction away from the cervical vertebrae support portion 120. With the inclination of the fourth ventricle expanding protrusion 111 and the cervical vertebrae support portion 120, the user's upper cervical vertebra is positioned to be highest, and the user's lower cervical vertebra and the user's occipital region are positioned to be lower than the upper cervical vertebra.

The occipital underlying crest b, which defines a boundary with the occipital region accommodating portion 110, is formed at an end of the cervical vertebrae support portion 120. Based on the occipital underlying crest b, the occipital region is positioned at one side, and the cervical vertebrae are positioned at the other side. The lower cervical vertebra is pulled downward due to a weight of the body, and the upper cervical vertebra is pulled toward the occipital region due to a weight of the occipital region. That is, the user's cervical vertebrae are pulled toward both sides of the upper cervical vertebra and the lower cervical vertebra, and as a result, tension is applied to the cervical vertebrae. This is called distraction as a physiotherapy term.

The fourth ventricle expanding protrusion 111 has a compressing oblique side 11s which abuts the user's external occipital protuberance 54, and a horizontal component length d2 of the compressing oblique side 11s may be between 85 millimeters and 115 millimeters.

The compressing oblique side 11s defines an inclined surface. The compressing oblique side 11s supports the external occipital protuberance 54. The length of 85 to 115 millimeters is a length which corresponds to a size which corresponds to the external occipital protuberance 54 and may interrupt the extension phase. Based on the horizontal surface, an angle Θ7 of the fourth ventricle expanding protrusion 111 may be between 25 degrees and 36 degrees.

The angle Θ7 of the compressing oblique side 11s may be between 25 degrees and 36 degrees. The angle Θ7 and the horizontal component length d2 of the compressing oblique side 11s are determined based on a length of the external occipital protuberance 54 and a shape of the occipital bone, and it is difficult to interrupt the extension phase if a length of the compressing oblique side 11s is excessively long or short or if an angle of the compressing oblique side 11s is excessively high or low. The lateral support portion 130 has the shoulder pressing surface 131 which is formed at a portion facing the user's shoulder and inclined to press the user's shoulder downward.

The functional pillow for manipulation therapy according to another exemplary embodiment of the present invention includes the occipital region accommodating portion 110 which accommodates and supports the occipital region, the cervical vertebrae support portion 120 which is formed to be inclined and supports the cervical vertebrae, and the lateral support portion 130 which supports the user's head when the user lies on his/her side and has the shoulder pressing surface 131 formed at a portion facing the user's shoulder and inclined to press the user's shoulder downward.

Since the shoulder pressing surface 131 presses the shoulder forward and toward the ground surface, a position of the lower cervical vertebra is fixed. That is, the lower cervical vertebra is fixed by fixing the shoulder even though the upper cervical vertebra is pulled toward the occipital region accommodating portion 110 due to a weight of the occipital region. Therefore, tension is applied to the cervical vertebrae, and the cervical vertebrae are distracted. The lateral support portion 130 has the shoulder pressing surface 131 which is formed at a portion facing the user's shoulder and inclined to press the user's shoulder downward, and a ratio between the angles Θ3, Θ4, and Θ5 of the shoulder pressing surface 131 and the angle Θ7 of the fourth ventricle expanding protrusion 111 may be 1:1.3 to 1:5.5 based on the horizontal surface.

If the angle ratio between the fourth ventricle expanding protrusion 111 and the shoulder pressing surface 131 is too large or small, force for fixing the shoulder may be decreased, the user's shoulder may be inconvenienced, or it may be difficult to interrupt the extension phase.

Figure 24A:
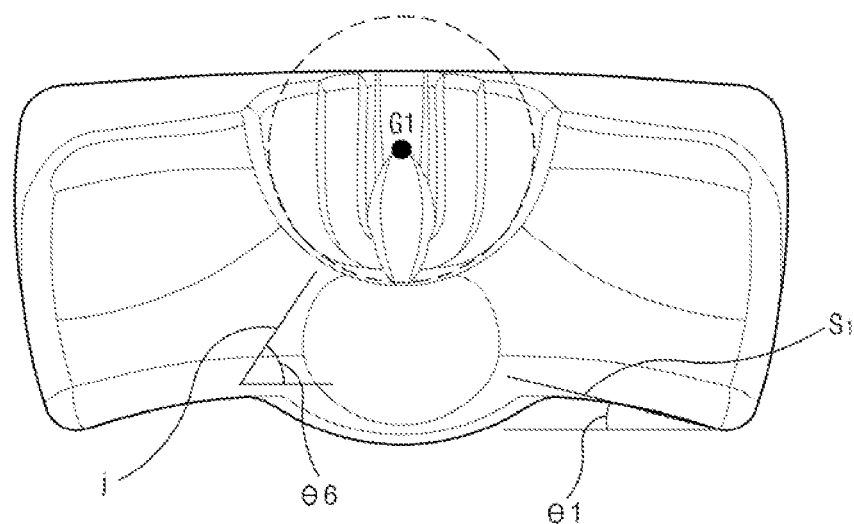
FIG. 24A is a view illustrating a position of an occipital region on the functional pillow for manipulation therapy according to another exemplary embodiment of the present invention when a user lies while looking at the top side.
Figure 24B:
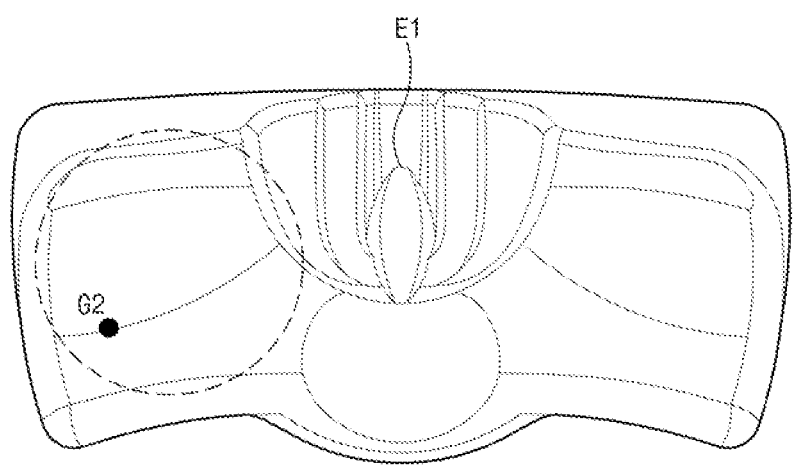
FIG. 24B is a view illustrating a position of a temporal region when the user lies on his/her side.
Figure 25A:
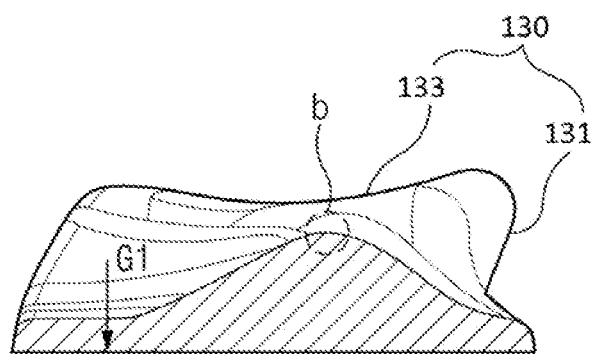
FIG. 25A is a view illustrating the position of the occipital region in FIG. 24A on a cross-sectional view taken along line A-A in FIG. 16A.
Figure 25B:
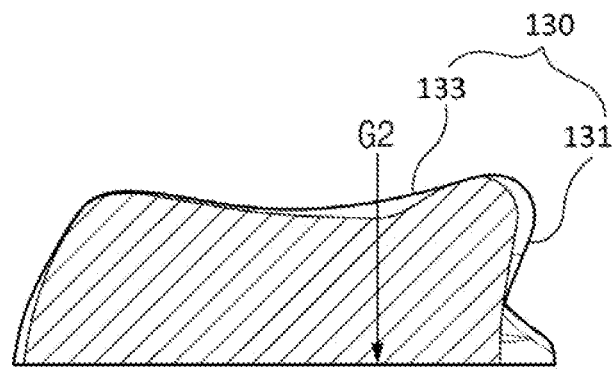
FIG. 25B is a view illustrating the position of the occipital region in FIG. 24B on a cross-sectional view taken along line P-P in FIG. 16A.

FIG. 24A is a view illustrating a position of the occipital region on the functional pillow for manipulation therapy according to another exemplary embodiment of the present invention when the user lies while looking at the top side, and FIG. 24B is a view illustrating a position of the temporal region when the user lies on his/her side. FIG. 25A is a view illustrating the position of the occipital region in FIG. 24A on a cross-sectional view taken along line A-A in FIG. 16A, and FIG. 25B is a view illustrating the position of the occipital region in FIG. 24B on a cross-sectional view taken along line P-P in FIG. 16A.

Referring to FIGS. 24A to 25B, a lowermost portion G2 of the upper surface of the lateral support portion 130 is formed further forward than a central portion G1 of the occipital region accommodating portion 110. The lowermost portion G2 of the upper surface of the lateral support portion 130 is formed further forward than a lowermost portion E1 of the fourth ventricle expanding protrusion 111.

A position of the central portion G1 of the occipital region accommodating portion 110 is an approximately rear end portion of the fourth ventricle expanding protrusion 111, and a lowermost portion G2 of the upper surface of the lateral support portion 130 is formed further forward than a central portion G1 of the occipital region accommodating portion 110. The central portion G1 of the occipital region accommodating portion may be a portion facing a center of gravity of the occipital region when the user lies while looking at the top side. The lowermost portion G2 of the upper surface of the lateral support portion 130 may be a portion facing a center of gravity of the temporal region when the user lies while looking at the lateral side.

Figure 26A:
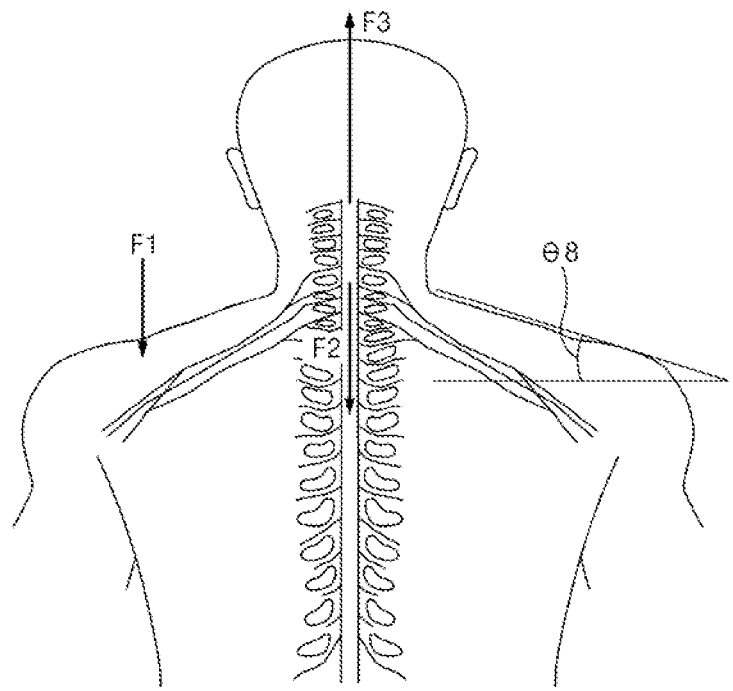
FIGS. 26A to 26B are a view illustrating a distraction effect of the functional pillow for manipulation therapy according to another exemplary embodiment of the present invention.
Figure 26B:
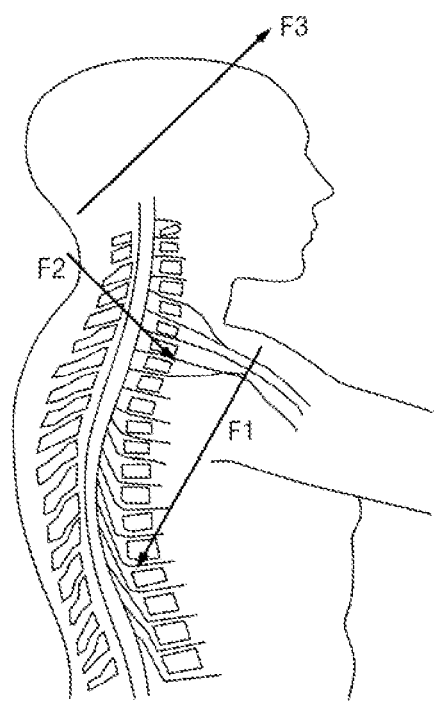
Figure 27:
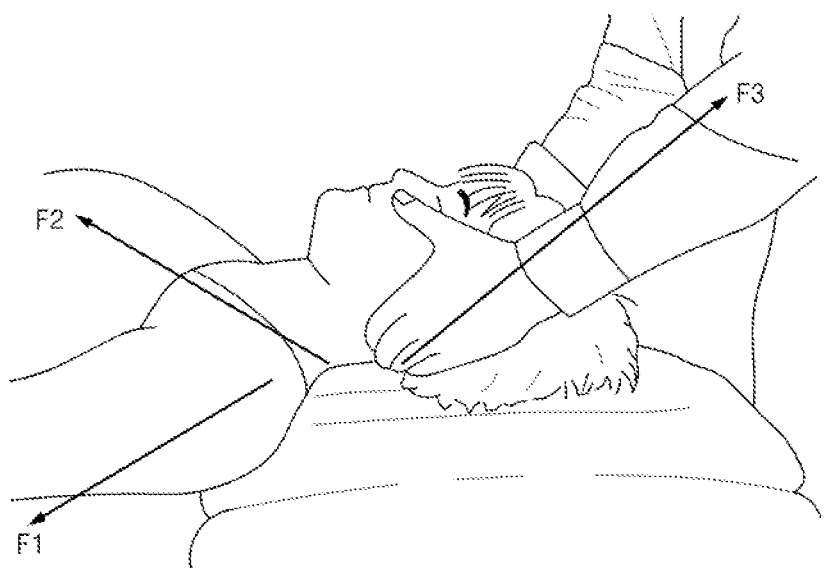
FIG. 27 is a view illustrating a procedure performed by a physical therapist in order to obtain the same distraction effect as the distraction effect of the functional pillow for manipulation therapy according to another exemplary embodiment of the present invention.

FIGS. 26A to 26B are a view illustrating a distraction effect of the functional pillow for manipulation therapy according to another exemplary embodiment of the present invention. FIG. 26A is a view illustrating a projection of the direction of force applied to the human body on the floor surface when the user lies while looking at the top side, and FIG. 26B is a view illustrating the projection of the direction of force applied to the human body on the lateral side when the user lies while looking at the top side. FIG. 27 is a view illustrating a procedure performed by a physical therapist in order to obtain the same distraction effect as the distraction effect of the functional pillow for manipulation therapy according to another exemplary embodiment of the present invention.

An effect of the functional pillow for manipulation therapy according to the exemplary embodiment of the present invention will be described below.

The functional pillow for manipulation therapy for the cervical vertebrae applies force to the human body in a total of approximately three directions. The force F1 is force that presses the shoulder forward and downward. F2 is force that pushes the cervical vertebrae forward and upward. F3 is force that pushes the occipital region rearward and upward. The shoulder pressing surface 131 may be made of an elastic material. The user's shoulder comes into close contact with the shoulder pressing surface 131, and the shoulder pressing surface 131 applies elastic force to the user's shoulder. The forces F1, F2, and F3 are generated by the elastic force of the shoulder pressing surface 131, a weight of the user's occipital region, and a weight of the cervical vertebrae.

A difference in direction between the forces F1 and F2 distracts the cervical vertebrae by pulling the cervical vertebrae upward and downward. In addition, a difference in direction among the forces F1, F2, and F3 distracts the cervical vertebrae by pulling the cervical vertebrae forward and rearward. In addition, since F1 presses the body in the direction toward the ground surface, F1 induces the user to sleep in an appropriate posture. Therefore, it is possible to obtain the same effect as the effect that may be obtained when the user is subjected to the manipulation therapy by a physical therapist in the related art.

In addition, referring to the drawings, because the user's shoulder line is inclined by an angle Θ8 and the upper end line S1 of the shoulder pressing surface 131 is also inclined, the user's shoulder may be uniformly pressed. That is, force applied to the shoulder is applied uniformly. In addition, it is possible to minimize interference even though the user lies on his/her side.

Figure 28:
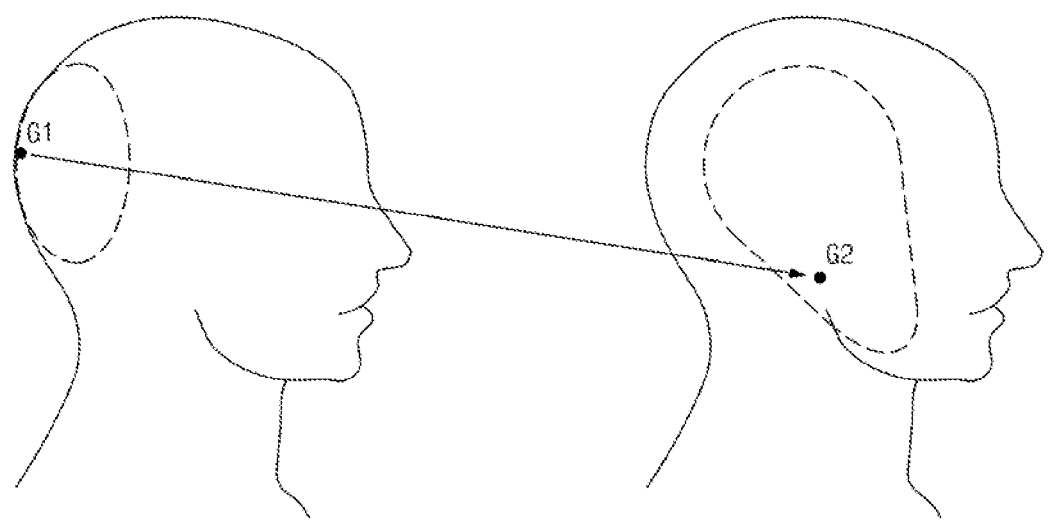
FIG. 28 is a view illustrating the changes from a position of the occipital region supported by the occipital region accommodating portion, and a center of gravity of the occipital region when the user lies while looking at the top side, to the position of the temporal region supported by the lateral support portion, and a center of gravity of the temporal region when the user lies while looking at a lateral side.

FIG. 28 is a view illustrating the changes from a position of the occipital region supported by the occipital region accommodating portion, and a center of gravity of the occipital region when the user lies while looking at the top side, to the position of the temporal region supported by the lateral support portion 130, and a center of gravity of the temporal region when the user lies while looking at a lateral side.

First, referring to FIG. 28, when the user sleeps while lying and looking at the top side, the user's occipital region is positioned on the occipital region accommodating portion 110. Therefore, the fourth ventricle compressing protrusion 113 stimulates the user's external occipital protuberance and induces the still point. Meanwhile, the cervical vertebrae support portion 120, the fourth ventricle compressing protrusion 113, and the shoulder pressing surface 131 produce an effect of correcting the cervical vertebrae by the distraction.

Next, the user may sleep while lying on his/her side. The user may prefer to sleep while lying on his/her side, and thus may sleep while lying on his/her side from the beginning, or the user may sleep while lying on his/her side unconsciously during sleep.

In this case, based on the user's head, a portion, which comes into contact with the functional pillow for manipulation therapy, is changed from the occipital region to the temporal region. The central portion G1 of the occipital region accommodating portion 110 and the lowermost portion G2 of the upper surface of the lateral support portion 130 are moved as illustrated in the drawings. However, according to the functional pillow for manipulation therapy according to the present invention, the position of the central portion G1 of the occipital region accommodating portion 110 recessed to accommodate the occipital region and the position of the lowermost portion G2 of the upper surface of the lateral support portion 130 recessed to support the temporal region are not present in the same line. That is, the temporal region accommodating portion 133 is formed further forward than the occipital region accommodating portion 110. Therefore, according to the pillow for correcting the cervical vertebrae by using distraction according to the exemplary embodiment of the present invention, it is possible to continuously and comfortably support the user even though the user changes his/her posture during sleep.

In addition, even though the user's jaws are formed to be inclined to have an angle, the lower jaw support crest j is formed to be inclined to correspond to a line of the user's jaws, and as a result, interference between the jaws and the functional pillow for manipulation therapy is minimized while the user's posture is changed.

While the exemplary embodiments of the present invention have been illustrated and described above, the exemplary embodiments of the present invention may be appropriately modified by those skilled in the art in accordance with the user's body build or body type. That is, the present invention may be modified in accordance with the user's age, the user's gender, the user's race, or the like. The present invention is not limited to the aforementioned specific exemplary embodiments, various modifications may be made by a person with ordinary skill in the technical field to which the present invention pertains without departing from the subject matters of the present invention that are claimed in the claims, and these modifications should not be appreciated individually from the technical spirit or prospect of the present invention.

What is claimed is:

1. A functional pillow for manipulation therapy, the functional pillow comprising:
    an occipital region accommodating portion which accommodates and supports an occipital region;
    a cervical vertebrae support portion which extends from the occipital region accommodating portion and supports cervical vertebrae;
    a fourth ventricle expanding protrusion which protrudes from the occipital region accommodating portion;
    an external shape forming portion which has a lateral support portion that extends in left and right directions from the occipital region accommodating portion, the cervical vertebrae support portion, the fourth ventricle compressing protrusion, and the occipital region accommodating portion; and
    a core portion which is disposed inside the external shape forming portion, and made of foam having higher hardness than that of the external shape forming portion,
    wherein the core portion includes a cervical vertebrae support core which is formed at a lower side of the cervical vertebrae support portion, an occipital region fixing core which is formed to avoid a lower side of the fourth ventricle compressing protrusion and formed at a lower side of an edge of the occipital region accommodating portion, and a lateral support core which extends from the occipital region fixing core and is formed at a lower side of the lateral support portion.

2. A functional pillow for manipulation therapy, the functional pillow comprising:
    an occipital region accommodating portion which accommodates and supports an occipital region;
    a cervical vertebrae support portion which is formed to be inclined and supports cervical vertebrae; and
    a lateral support portion which is formed at left and right sides of the cervical vertebrae support portion and the occipital region accommodating portion, and supports a user's head when the user lies on his/her side,
    wherein the cervical vertebrae support portion is inclined rearward so that a height of the cervical vertebrae support portion is increased in a direction from the user's lower cervical vertebra to the user's upper cervical vertebra, the lateral support portion has shoulder pressing surface which is inclined forward at a portion facing the user's shoulder and inclined to press the user's shoulder downward, the shoulder pressing surface extends from the cervical vertebrae support portion in left and right directions such that based on a horizontal surface, a gradient of the shoulder pressing surface is gradually decreased in a direction away from the cervical vertebrae support portion, and the gradient of the shoulder pressing surface is between 89 to 75 degrees.

3. A functional pillow for manipulation therapy, the functional pillow comprising:
    an occipital region accommodating portion which accommodates and supports an occipital region;
    a cervical vertebrae support portion which is formed to be inclined and supports cervical vertebrae;
    a lateral support portion which is formed at left and right sides of the cervical vertebrae support portion and the occipital region accommodating portion, and supports a user's head when the user lies on his/her side; and a fourth ventricle expanding protrusion which protrudes from the occipital region accommodating portion and inclines in a direction opposite to a direction in which the cervical vertebrae support portion is inclined, wherein the fourth ventricle expanding protrusion has a compressing oblique side that abuts the user's external occipital protuberance, a horizontal component length of the compressing oblique side is between 80 millimeters and 120 millimeters, and an angle of the fourth ventricle expanding protrusion is between 25 degrees and 36 degrees based on a horizontal surface.

4. A functional pillow for manipulation therapy, the functional pillow comprising:

an occipital region accommodating portion which accommodates and supports an occipital region;

a cervical vertebrae support portion which is formed to be inclined and supports cervical vertebrae;

a lateral support portion which is formed at left and right sides of the cervical vertebrae support portion and the occipital region accommodating portion, and supports a user's head when the user lies on his/her side; and a fourth ventricle expanding protrusion which protrudes from the occipital region accommodating portion and inclines in a direction opposite to a direction in which the cervical vertebrae support portion is inclined, wherein a lowermost portion of an upper surface of the lateral support portion is formed further forward than a lowermost portion of the fourth ventricle expanding protrusion, wherein the lateral support portion has shoulder pressing surface which is formed at a portion facing the user's shoulder and inclined to press the user's shoulder downward, and wherein—a ratio between an angle of the shoulder pressing surface and an angle of the fourth ventricle expanding protrusion is 1:1.3 to 1:5.5 based on a horizontal surface.

5. A functional pillow for manipulation therapy, the functional pillow comprising:

an occipital region accommodating portion which accommodates and supports an occipital region;

a cervical vertebrae support portion which is formed to be inclined and supports cervical vertebrae;

a lateral support portion which is formed at left and right sides of the cervical vertebrae support portion and the occipital region accommodating portion, and supports a user's head when the user lies on his/her side; and a fourth ventricle expanding protrusion which protrudes from the occipital region accommodating portion and inclines in a direction opposite to a direction in which the cervical vertebrae support portion is inclined, wherein a lowermost portion of an upper surface of the lateral support portion is formed further forward than a lowermost portion of the fourth ventricle expanding protrusion, wherein the lateral support portion has shoulder pressing surface which is formed at a portion facing the user's shoulder and inclined to press the user's shoulder downward, and wherein the fourth ventricle expanding protrusion extends from the cervical vertebrae support portion, and a width between a first horizontal line which meets a start point of the fourth ventricle expanding protrusion and a second horizontal line which abuts an upper end line of the shoulder pressing surface is between 80 millimeters and 130 millimeters among a plurality of horizontal lines perpendicular to a longitudinal direction of the fourth ventricle expanding protrusion.

6. A functional pillow for manipulation therapy, the functional pillow comprising:

an occipital region accommodating portion which accommodates and supports an occipital region;

a cervical vertebrae support portion which is formed to be inclined and supports cervical vertebrae;

a lateral support portion which is formed at left and right sides of the cervical vertebrae support portion and the occipital region accommodating portion, and supports a user's head when the user lies on his/her side; and a fourth ventricle expanding protrusion which protrudes from the occipital region accommodating portion and inclines in a direction opposite to a direction in which the cervical vertebrae support portion is inclined, wherein a lowermost portion of an upper surface of the lateral support portion is formed further forward than a lowermost portion of the fourth ventricle expanding protrusion, wherein the lateral support portion has shoulder pressing surface which is formed at a portion facing the user's shoulder and inclined to press the user's shoulder downward, and wherein the fourth ventricle expanding protrusion extends from the cervical vertebrae support portion, an angle between the shoulder pressing surface and any one of a plurality of horizontal lines perpendicular to a longitudinal direction of the fourth ventricle expanding protrusion is gradually increased from a lower end line of the shoulder pressing surface to an upper end line of the shoulder pressing surface, an angle between the lower end line of the shoulder pressing surface and the horizontal line is 1 to 7 degrees, and an angle between the upper end line of the shoulder pressing surface and the first horizontal line is 8 to 15 degrees.

7. A functional pillow for manipulation therapy, the functional pillow comprising:

an occipital region accommodating portion which accommodates and supports an occipital region;

a cervical vertebrae support portion which is formed to be inclined and supports cervical vertebrae;

a lateral support portion which is formed at left and right sides of the cervical vertebrae support portion and the occipital region accommodating portion, and supports a user's head when the user lies on his/her side; and a fourth ventricle expanding protrusion which protrudes from the occipital region accommodating portion and inclines in a direction opposite to a direction in which the cervical vertebrae support portion is inclined, wherein a lowermost portion of an upper surface of the lateral support portion is formed further forward than a lowermost portion of the fourth ventricle expanding protrusion, and wherein the cervical vertebrae support portion has a cervical vertebrae accommodating groove which accommodates the user's cervical vertebrae, a lower jaw support crest is formed to define a boundary between the cervical vertebrae accommodating groove and the lateral support portion, and an angle between the lower jaw support crest and any one of a plurality of horizontal lines perpendicular to a longitudinal direction of the fourth ventricle expanding protrusion is 40 to 65 degrees.

* * * * *